US010154673B2

(12) United States Patent
Dodd et al.

(10) Patent No.: US 10,154,673 B2
(45) Date of Patent: Dec. 18, 2018

(54) METHOD OF REMOVING LACTOSE FROM A SOLUTION

(71) Applicant: Stellenbosch University, Stellenbosch (Western Cape) (ZA)

(72) Inventors: Amanda Jane Dodd, Dusseldorf (DE); Lubertus Klumperman, Leiderdorp (NL); Pieter Swart, Stellenbosch (ZA)

(73) Assignee: STELLENBOSCH UNIVERSITY, Western Cape Province (ZA)

( * ) Notice: Subject to any disclaimer, the term of this patent is extended or adjusted under 35 U.S.C. 154(b) by 0 days.

(21) Appl. No.: 15/113,053

(22) PCT Filed: Jan. 27, 2015

(86) PCT No.: PCT/IB2015/050618
§ 371 (c)(1),
(2) Date: Jul. 21, 2016

(87) PCT Pub. No.: WO2015/111030
PCT Pub. Date: Jul. 30, 2015

(65) Prior Publication Data
US 2016/0330988 A1 Nov. 17, 2016

(30) Foreign Application Priority Data

Jan. 27, 2014 (ZA) .................. 2014/00633

(51) Int. Cl.
*A23C 9/12* (2006.01)
*B03C 1/30* (2006.01)
*G01N 33/543* (2006.01)

(52) U.S. Cl.
CPC .............. *A23C 9/1206* (2013.01); *B03C 1/30* (2013.01); *G01N 33/54326* (2013.01); *A23C 2220/104* (2013.01); *A23C 2220/106* (2013.01); *A23V 2002/00* (2013.01); *A23V 2300/28* (2013.01); *B03C 2201/18* (2013.01); *B03C 2201/20* (2013.01); *G01N 2333/938* (2013.01)

(58) Field of Classification Search
CPC ........... A23C 9/1206; A23C 2220/104; A23C 2220/106; B03C 1/30; B03C 2201/18; B03C 2201/20; G01N 33/54326
USPC ..................... 426/36, 41; 435/207
See application file for complete search history.

(56) References Cited

PUBLICATIONS

Akbarzadeh A et al. in Nanoscale Research Letters. 7: 144, 2012. (Year: 2012).*
Pessela BCC et al. in Biomacromolecules 4: 107-113, 2003. (Year: 2003).*
Safarik I et al. in Biomagnetic Research and Technology 2: 7, 2004 pp. 1-14 (Year: 2004).*
International Preliminary Report on Patentability issued in corresponding International Patent Application No. PCT/IB2015/050618 dated Aug. 2, 2016 (6 pages).
International Search Report issued in corresponding International Patent Application No. PCT/IB2015/050618 dated Aug. 7, 2015 (4 pages).
Bayramoglu et al., "Immobilization of beta-galactosidase onto magnetic poly(GMA-MMA) beads for hydrolysis of lactose in bed reactor," Catalysis Communications, vol. 8, No. 7, 2007, pp. 1094-1101.
Neri et al., "Immobilization of beta-galactosidase from Kluyveromyces lactis onto a polysiloxane-polyvinyl alcohol magnetic (mPOS-PVA) composite of lactose hydrolysis," Catalysis Communications, vol. 9, No. 14, 2008, pp. 2334-2339.
Neri et al., "Galactooligosaccharides production by beta-galactosidase immobilized onto magnetic polysiloxane-polyaniline particles," Reactive & Functional Polymers, vol. 69, No. 4, 2009, pp. 246-251.
Yuan et al., "Substitutions for Glu-537 of beta-galactosidase from *Escherichia coli* cause large descreases in catalytic activity," Biochem. J., vol. 299, 1994, pp. 527-531.

* cited by examiner

Primary Examiner — Bhaskar Mukhopadhyay
(74) Attorney, Agent, or Firm — Kilyk & Bowersox, P.L.L.C.

(57) ABSTRACT

The invention provides protein-functionalized magnetic nanoparticles comprising magnetic nanoparticles (MNPs) to which a lactose-binding protein or enzyme has been immobilized. The protein-functionalized magnetic nanoparticles are particularly suitable for separating lactose from a lactose-containing solution, such as milk, cheese, yoghurt, flavored milk or the like. The protein-functionalized MNPs can be added to the lactose-containing solution and be allowed to bind to the lactose in the solution. The MNPs, to which the lactose is bound, can then be magnetically removed from the solution, e.g. by applying an external magnetic field.

12 Claims, 21 Drawing Sheets
Specification includes a Sequence Listing.

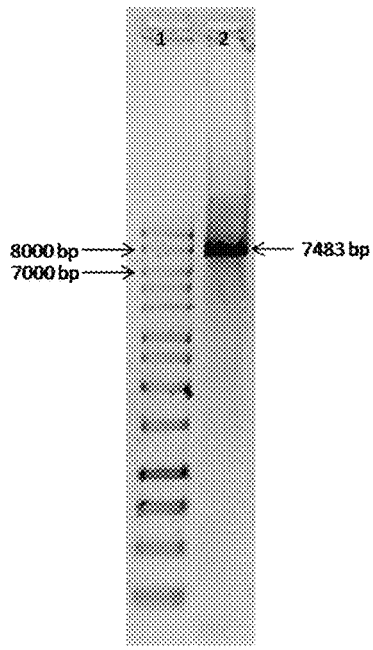

Figure 12

```
       1930      1940      1950      1960      1970      1980      1990      2000
    ....|....|....|....|....|....|....|....|....|....|....|....|....|....|....|....|
    TAATCACGACGCCGCTGTATCGCTGGATCAAATCTGTCGATCCTTCCCGCCCGGTGCAGTATGAAGGCGGCGCACCCGACA 2010      2020      2030      2040      2050      2060      2070      2080
    ....|....|....|....|....|....|....|....|....|....|....|....|....|....|....|....|
    CCACCGCCACCGATATTATTTGCCCGATGTACGCGCGCGTGGATGAAGACCAGCCCTTCCCGGCTGTGCCGAAATGGTCC 2090      2100      2110      2120      2130      2140      2150      2160
    ....|....|....|....|....|....|....|....|....|....|....|....|....|....|....|....|
    ATCAAAAAATGGCTTTCGCTACCTGGAGAGACCGCGCCCGCTGATCCTTTGCGACTACGCCCACGCGATGGGTAACAGTCT 2170      2180      2190      2200      2210      2220      2230      2240
    ....|....|....|....|....|....|....|....|....|....|....|....|....|....|....|....|
    TGGCGGTTTCGCTAAATACTGCGCAGGCGTTTCGTCAGTATCCCCGTTTACAGGGCGGCTTCGTCTGCGACTGGGTGGATC 2250      2260      2270      2280      2290      2300      2310      2320
    ....|....|....|....|....|....|....|....|....|....|....|....|....|....|....|....|
    AGTCGCTGATTAAATATGATGAAAACGGCAACCCGTGGTCGGCTTACGGCGGTGATTTTGGCGATACGCCGAACGATCGC 2330      2340      2350      2360      2370      2380      2390      2400
    ....|....|....|....|....|....|....|....|....|....|....|....|....|....|....|....|
    CAGTTCTGTATGAACGGTCTGGTCTTTGCCGACCGCACGCCGCATCCAGCGCTGACGGAAGCAAAACACCAGCAGCAGTT
```

Figure 13

METHOD OF REMOVING LACTOSE FROM A SOLUTION

CROSS-REFERENCE TO RELATED APPLICATIONS

This application claims priority to South African provisional patent application number 2014/00633, which is incorporated by reference herein.

FIELD OF THE INVENTION

The invention relates to a method of separating lactose from a solution, such as milk, using magnetic nanoparticles functionalised with a lactose-binding protein and a magnetic field.

BACKGROUND TO THE INVENTION

Lactose intolerance (also known as hypolactasia) is a condition that affects approximately 70% of the world's population and symptoms include bloating, flatulence and diarrhoea. It is caused by the inability to digest lactose due to the down regulation of the enzyme lactase. As a result, lactose is not digested by the body and passes into the colon where it is fermented by gut bacteria into fatty acids and various gases, the most notable being hydrogen. Milk contains 4-6 g lactose/100 ml, but because it provides a very rich source of calcium and vitamin C, lactose free milk and milk products are in high demand. These products contain less than 0.25 g lactose/100 ml of milk and are produced by the hydrolysis of lactose into its two monomers, galactose and glucose, by the enzyme lactase ($\beta$-galactosidase).

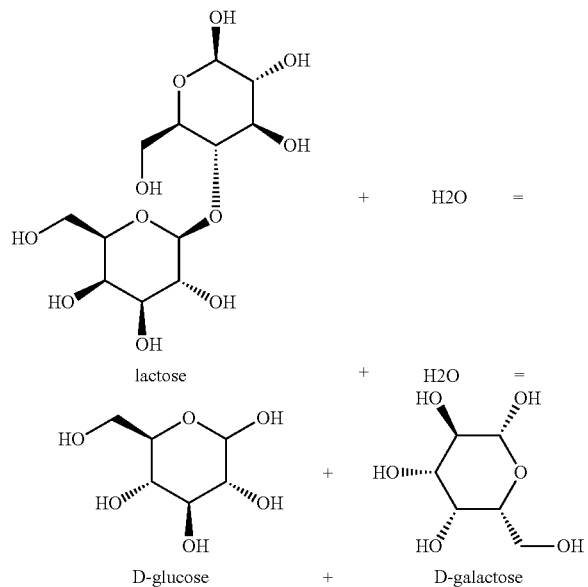

Hydrolysis Reaction of $\beta$-Galactosidase. Lactose is Hydrolysed into Galactose and Glucose However, lactose free milk is generally regarded by consumers as having an unsatisfactory taste compared to normal milk. This may be attributed to the increased sweetness of the lactose free milk, created by the hydrolysis of lactose to galactose and glucose. Lactose has a relatively low sweetness and solubility, whereas galactose and glucose are much sweeter, resulting in the lactose free milk being much sweeter than normal milk.

There is therefore a need for an alternative method of producing lactose-free milk.

SUMMARY OF THE INVENTION

According to a first embodiment of the invention, there is provided a protein-functionalised magnetic nanoparticle which comprises a magnetic nanoparticle onto which a lactose-binding protein is immobilised.

The lactose-binding protein may be $\beta$-galactosidase, such as from E. coli.

The protein-functionalised magnetic nanoparticle may be capable of binding to lactose which is present in a solution, such as milk or a dairy product.

The protein-functionalised magnetic nanoparticle may be capable of being magnetically separated from a solution.

The $\beta$-galactosidase may contain at least one mutation which reduces the lactose hydrolysing activity of the $\beta$-galactosidase relative to the wildtype $\beta$-galactosidase. The mutation may be an E537D mutation or any other mutation which reduces the lactose hydrolysing activity of the enzyme without reducing its lactose-binding capability.

The lactose-binding protein may have an affinity tag at or near the N- or C-terminus.

The affinity tag may be selected from the group consisting of a polyhistidine tag (His-tag), a transglutaminase, a glutathione S-transferase, a FLAG, a biotin, a maltose binding protein, a glycoprotein and a cysteine-mediated site-directed mutagenesis product.

The magnetic nanoparticle may have a coating.

The lactose-binding protein may be immobilised on the magnetic nanoparticle by way of at least one bond or interaction selected from the group consisting of covalent bonds, electrostatic interactions, coordination bonds, ionic bonds, hydrophobic interactions, affinity links and hydrophilic interactions.

According to a second embodiment of the invention, there is provided a method for separating lactose from a lactose-containing solution, the method comprising the steps of:
  adding to the solution magnetic nanoparticles to which a lactose-binding protein is immobilised;
  allowing the protein on the magnetic nanoparticles to bind to lactose in the solution; and
  removing the magnetic nanoparticles from the solution.

The method may result in no substantial increase or decrease of the sweetness of the solution by removal of the lactose.

According to a third embodiment of the invention, there is provided a method of making a protein-functionalised magnetic nanoparticle as described above, the method comprising the steps of:
  i. immobilising a lactose-binding protein on a magnetic nanoparticle; and
  ii. stabilising or protecting the magnetic nanoparticle, either before or after immobilising the lactose-binding protein.

The lactose-binding protein may be immobilised on the magnetic nanoparticles randomly, e.g. by adsorption or chemical reactions, or in a controlled manner by directed immobilisation, e.g. by immobilised metal affinity chromatography (IMAC). Covalent or non-covalent interactions may be created between the protein and the magnetic nanoparticles.

According to a fourth embodiment of the invention, there is provided a dairy product with a reduced lactose content compared to a normal dairy products, wherein lactose has been removed from the dairy product by the method substantially as described above.

BRIEF DESCRIPTION OF THE FIGURES

FIG. 12: Agarose gel in TAE buffer representing the mutagenesis reaction of the lacZ gene. Lane 1: 1 kb DNA ladder (Promega), Lane 2: 7483 bp Mutagenesis reaction product.

FIG. 13: Portion of the nucleotide sequence of the pTrcHis-lacZ plasmid (SEQ ID NO: 7). The nucleotide at position 2139 represents the location of the E537D mutation present within the pTrcHis-lacZ plasmid.

DETAILED DESCRIPTION OF THE INVENTION

Figure 1:
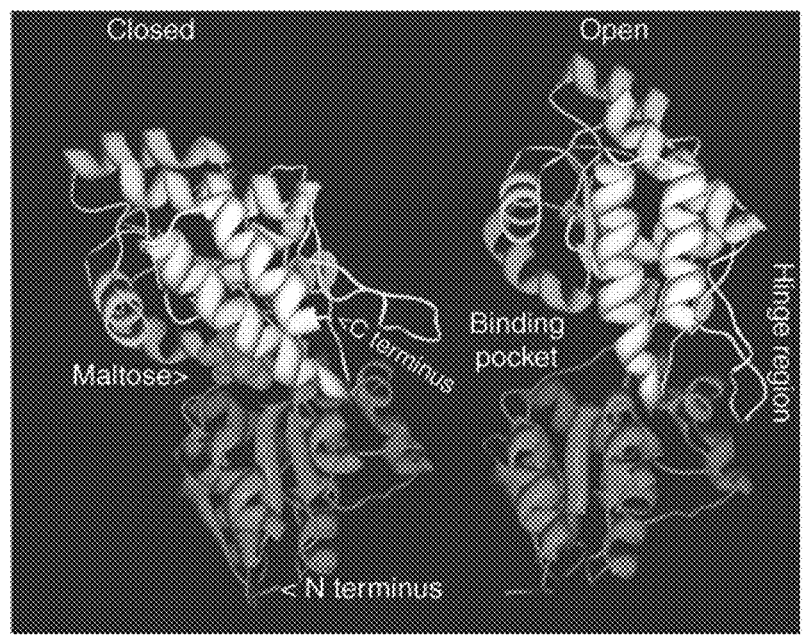
FIG. 1: 3D Structure of maltose binding protein (MBP). MBP has two domains connected by a hinge region which allows it to move between an open (ligand free) and closed (ligand bound) conformation (1).

Magnetic nanoparticles to which a lactose-binding protein or enzyme is immobilised are described herein, in particular for use in separating lactose from a lactose-containing solution. The protein-functionalised magnetic nanoparticles can be added to a solution containing lactose, such as milk or a milk or dairy product, and the protein is allowed to bind to the lactose in the solution. The magnetic nanoparticles (MNPs), to which the lactose is bound, can be magnetically removed from the solution, e.g. by applying an external magnetic field.

The method can also include the steps of protecting and stabilising the MNPs and/or immobilising the enzyme on the MNPs, in either order, prior to adding them to the solution.

The milk or dairy product can be cheese, yoghurt, flavoured milk or the like.

As used herein, the term "lactose-free" refers to a solution which comprises a reduced amount of lactose compared to a naturally occurring solution, such as less than 40%, less than 50% less than 75% or even less than 90%. More particularly, the solution contains less than 1 g lactose/100 ml, and even more preferably less than 0.5 g lactose/100 ml or less than 0.25 g lactose/100 ml.

The MNPs can be manufactured by any one of several methods which are well-known in the art, or may be purchased from commercial suppliers. They are usually made from iron oxides and, as the name indicates, are attracted to and can be manipulated by an external magnetic field (2-4). They can thus be simply removed from a solution. MNPs need to be protected as they are inherently unstable when uncoated. There are two broadly defined ways to protect the particles: the first method is to coat the MNPs with organic shells such as surfactants, polymers and biomolecules. The other method is to coat them with an inorganic layer such as silica and metals (5). The protection and stabilisation of MNPs also functionalises the MNPs to create their specific applications. MNPs can be functionalised with a wide variety of biomolecules and can take place via similar methods as for protein immobilisation. These include covalent and non-covalent methods and the use of affinity tags (2). Non-covalent functionalisation depends on hydrophobic/hydrophilic and ionic interactions and can take place either on the MNP itself, without a coating, or with the use of a coating (6). Covalent functionalisation can take place either through an active group that is on the MNP's surface, a functionalised group on the protein itself or between both (6). Examples of commercially available magnetic nanoparticles are DynaBeads™ from Invitrogen and FluidMAG-Q™ and Fluid-MAG-DXS™ from Chemicell GmbH.

The lactose-binding enzyme can be β-galactosidase (β-gal). β-gal (EC 3.2.1.23) is the enzyme responsible for the hydrolysis of D-galactosyl residues, oligosaccharides or secondary metabolites (7). It is present in a large variety of organisms including yeast (e.g. *Kluyveromyces fragilis, Kluyveromyces lactis, Saccharomyces lactis, Saccharomyces anamensis* and *K. marxiana*), fungi (e.g. *Aspergillus oryzae*) and bacteria (e.g. *Streptococci, Lactococci, Lactobacilli*, and *E. coli*) (8-10). In one embodiment of the invention, the β-gal originates from *E. coli*. In *E. coli* β-gal is the product of the lacZ gene and consists of 1023 amino acids per monomer (11). The active form of β-gal is tetrameric with a molecular weight of 464 kDa (each subunit has a mass of 116 kDa). This tetrameric form has four active sites but the enzyme does not exhibit cooperativity. Three active site residues are responsible for the hydrolysis of lactose, Glu537, Glu461 and His418. The β-gal can contain one or more mutations, in particular to reduce the lactose hydrolysis activity of the enzyme. The mutation, however, should still retain the lactose-binding capacity of the enzyme. For example, the β-galactosidase can be an E537D, E537Q or E537V mutant.

The lactose-binding enzyme can be immobilised on the magnetic nanoparticles randomly, e.g. by adsorption or chemical reactions, or in a controlled manner by directed immobilisation, e.g. by IMAC. Physical adsorption relies on several weak interactions such as hydrophobic/hydrophilic, electrostatic and van der Waals forces (12). The adsorption of an enzyme onto a functionalised surface requires multiple interaction points of the enzyme and different sites for binding on the solid support. (13).

The enzyme can be covalently immobilised onto the solid support by methods which are well known to a person skilled in the art. For example, the support can be activated with tosyl chloride, cyanogen bromide, glutaraldehyde or 1-ethyl-3-(3-dimethylaminopropyl) carbodiimide (EDC). A chemical reaction with a functional group within the enzyme can then take place, such as those listed in Table 1. The functional group used for immobilisation should be unimportant and abundant in the protein so as to produce a variety of points of attachment. Additionally, the reaction should take place with a substrate or substrate analogue present to protect the active site of the protein and to result in the random orientation of the protein (8).

TABLE 1

Summary of the chemical reactions that take place in order to achieve covalent immobilisation of proteins onto a solid support (14)

| Immobilisation method | Amino acid | Functional group | Reaction |
| --- | --- | --- | --- |
| Diazotisation | ε-amino group of lysine<br>N-terminal amino acid<br>Tyrosine<br>Histidine | Amino<br>Phenol<br>Imidazole | —N=N-Protein |
| Peptide bond formation | ε-amino group of lysine<br>N-terminal amino acid<br>Aspartic acid<br>Glutamic acid | Amino<br>Carboxyl group | $\overset{O}{\underset{}{\overset{\|}{-C}}}$—NH-Protein |
| Arylation | ε-amino group of lysine<br>N-terminal amino acid | Amino | —NH-Protein |
| Alkylation | ε-amino group of lysine<br>N-terminal amino acid<br>Cysteine | Amino<br>Sulfhydryl | —$CH_2$—NH-Protein<br>—$CH_2$—SH-Protein |
| Schiff-base formation | ε-amino group of lysine<br>N-terminal amino acid | Amino | —CH=N-Protein |
| Amidination | ε-amino group of lysine<br>N-terminal amino acid | Amino | $\overset{NH_2^+}{\underset{}{\overset{\|}{-C}}}$—NH-Protein |
| Thio-disulfide interchange | Cysteine | Sulfhydryl | —S—S-Protein |

Site-directed mutagenesis is used to immobilise proteins in a site specific way. The tertiary structure should preferably be known and the gene encoding for the protein needs to be cloned into a host system where genetic manipulations are possible (13, 15). The addition of affinity tags to proteins on either the N- or C-terminal allows for some control over the orientation of the protein on the solid support. Affinity tags include transglutaminase (16, 17), glutathione S-transferases (15, 18), FLAG (13, 15, 18), biotinylation (5, 12, 15, 19, 20), immobilised metal affinity chromatography (12, 15, 21, 22), maltose binding protein (15), glycoproteins (12) and cysteine mediated site directed mutagenesis.

Immobilisation of the lactose-binding protein onto MNPs can lead to improved stability as well as activity of the protein. Other desirable features are that the enzyme does not remain in the solution in which it was functioning, the protein-functionalised MNPS can be used more than once, control over product formation is possible, processes are simplified and continuous operations can be implemented. Moreover, MNPs have a high surface to volume ratio, high sensitivity and accuracy, can be easily transported and are relatively inexpensive.

Removal of Maltose from Solution with Maltose Binding Protein Functionalised Magnetic Nanoparticles To demonstrate that functionalised magnetic nanoparticles (MNPs) can be used as a bioseperation technique, a proof of principle experiment was conducted. Maltose was removed from solution with the aid of maltose binding protein (MBP) functionalised MNPs, demonstrating that it is possible to remove a disaccharide from solution, with the ultimate aim being to remove lactose from solution.

Magnetic Nanoparticles

Figure 33A:
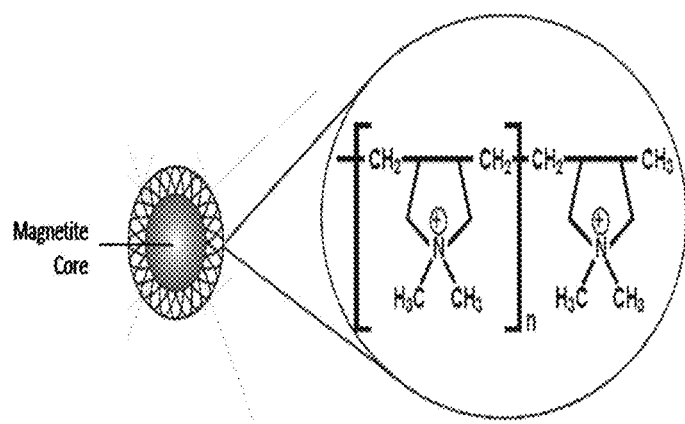
FIG. 33A: FluidMAG-Q MNPs with the Poly(diallyldimethylammonium chloride) matrix which supplies the MNPs with a positive charge.
Figure 33B:
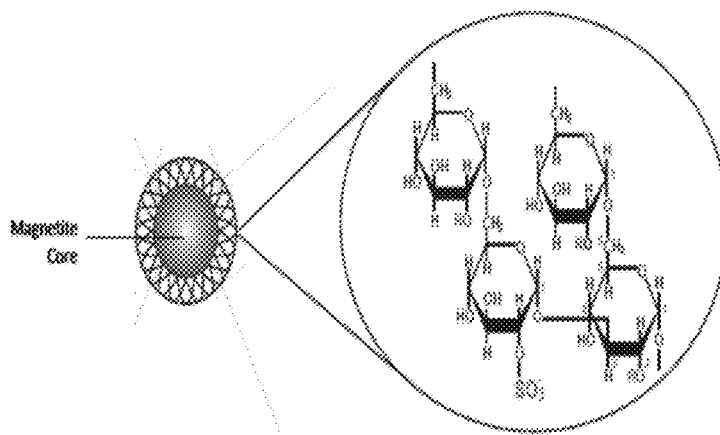
FIG. 33B: FluidMAG-DXS MNPS with the dextransulfate matrix which supplies the MNPs with a negative charge.

There are several MNPs on the market that allow for functionalisation. FluidMAG MNPs from Chemicell GmbH (Germany) were utilised as the solid support for MBP immobilisation in this study. The fluidMAG MNPs have terminal functionalities that can act as ion exchangers or reactive groups for use in covalent modification. This study made use of the ion exchange functionality; specifically fluidMAG-Q, which is a strong anion exchanger and fluidMAG-DXS, which is a strong cation exchanger. The fluidMAG-Q MNPs have a diameter of a 100 nm, a 50 mg/ml weight of volume and a surrounding matrix of Poly(diallyldimethylammonium chloride), whereas the fluidMAG-DXS have a 25 mg/ml weight of volume and a matrix of dextran sulphate (FIGS. 33A and 33B).

Maltose Binding Protein

Maltose binding protein (MBP) was chosen to further functionalise the fluidMAG MNPs. MBP is a maltose transport protein found in E. coli. It has a molecular weight of 42.5 kDa, a pI of 5.1 and is stable in the pH range from 4 to 10.5. MBP belongs to the family of ATC-binding cassettes. MBP consists of two domains that are connected by a hinge region which allows for two conformations. The first conformation is the open conformation in which no ligand is bound. The second conformation is a closed one where ligand is bound (FIG. 1) (23).

To utilise MBP with the fluidMAG MNPs, MBP can be manipulated to carry a net positive or negative charge depending on the pH of its environment. This principle was used as the immobilisation technique for MBP on the MNPs. If the pH was to be set lower than the pI of MBP it would adopt a net positive charge and be able to undergo electrostatic interactions with the fluidMAG-DXS MNPs. If the pH was to be set higher than the pI of MBP it would adopt a net negative charge and bind to the fluidMAG-Q MNPs. Once bound to the MNPs it was hypothesized that the MBP functionalised MNPs would bind maltose. With the use of an external magnetic field (3) it should be possible to remove maltose, along with the MBP functionalised MNPs, from solution.

Due to MBP's 3D structure, loss of function was a potential problem associated with immobilisation on MNPs. The immobilisation of MBP in this case was chosen to be random to provide many varying protein orientations, some of which would retain the maltose binding function.

Cloning, Site Directed Mutagenesis and Characterisation of His-Tagged *Escherichia coli* β-Galactosidase After confirming that it was possible to remove a disaccharide from solution using protein immobilised MNPs, lactose was removed from solution. Lactose binding lectins are not common and are difficult to attain for experimental purposes. Lactose binding lectins are often found in animal tissue such as the electric eel, earthworm, chicken, hamster and frog and have a wide variety of functions within each animal.

A mutated form of the *E. coli* enzyme β-gal was used in this study as it is easy to express in large quantities, is readily obtainable and lactose is its natural substrate (24). Three active site residues in *E. coli* β-gal are responsible for the catalysis of lactose. They are Glu537, Glu461 and His418 (25-29). In 1994 Yuan et al (11) reported three mutations in these active site residues. They were E537D, E537Q and E537V. Each of these mutants showed a decreased activity towards the artificial substrates ONPG (o-Nitrophenyl β-D-galactopyranoside) and PNPG (p-Nitrophenyl β-D-galactopyranoside). The E537D mutant was of interest in this study as it had a decreased activity but not to the same extent as the other mutants. This characteristic was of importance as the residual galactosidase activity of the enzyme would create a small amount of glucose to sweeten the milk slightly and compensate for the loss of lactose, making the resulting milk more acceptable to consumers than unsweetened lactose-free milk or milk with a high glucose content (lactose does sweeten milk to a certain extent, and if it is fully removed it may also be dissatisfying to consumers). The remaining lactose could be removed in the same step.

An N-terminal His-tag was added to β-gal to allow for a fast and easy purification with IMAC and to provide a tag to allow for directed immobilisation of β-gal onto the MNPs. Site-directed mutagenesis was performed in order to replace the Glu537 residue with an aspartic acid (Asp) residue and create the E537D mutant.

Once β-gal had been cloned to contain an N-terminal His-tag and mutated to form the E537D mutant, it was determined whether it was possible to express and purify β-gal (both wildtype and mutant) in sufficient quantities. The proteins were purified using IMAC since both the wildtype and mutant contained an N-terminal His-tag. Once expressed and purified, the kinetic and binding characteristics of the two enzymes were determined.

IMAC

Figure 34:
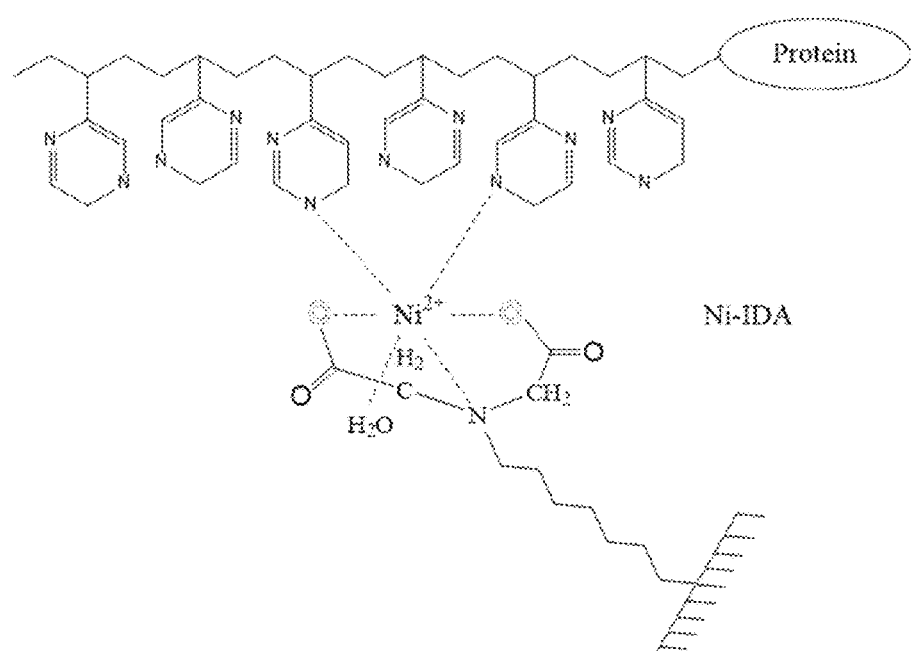
FIG. 34: Diagrammatic representation of the interaction of a His-tag with a Ni-IDA affinity matrix (31).

Immobilised metal affinity chromatography (IMAC) is a popular and widely applied technique (21, 22). Histidine (His) has a very high affinity for transition metals and as a result has been developed as an affinity tag. His-tags can be incorporated onto either the N- or C-terminal of a protein. The imidazole moiety of the His residue forms coordination bonds, via its electron donor group, with the transition metals as shown below (30) FIG. 34).

His-tags possess a very high affinity for $Ni^{2+}$, $Co^{2+}$, $Cu^{2+}$, $Zn^{2+}$ and $Fe^{2+}$ (the $K_d$ can be as low as $10^{-13}$ M) and can been fused to a target protein (12, 15, 21, 22, 24, 32-34). The most common His-tag consists of six His residues which can be attached to either the N- or C-terminal of a protein. Other His-tag sequences include 8, 10 and 14 His residues as well as His rich sequences interspaced by other amino acid residues (31). The affinity matrix consists of a chelating agent which is able to immobilise the transition metal ions and present it for protein binding (15). The chelating agent is usually a tetradentate resin and the most common one used is nitrilotriacetic acid (NTA). Iminodiacetic acid (IDA), which is tridentate, is also used (30, 31).

IMAC operates at very mild and non-denaturing conditions and purification of single proteins from complex mixtures can be performed in a single step. Compared to the use of antibodies and enzymes as a solid support for affinity chromatography, the immobilised metal ions tend to last longer and are easily regenerated. It is also possible to scale up IMAC for semi-preparative isolations and it can be used for molecules of a variety of molecular weights (30-31). Since IMAC is not affected by detergents it can be operated under denaturing conditions for the purification of aggregated proteins (15). IMAC offers a relatively simple, efficient and cost effective manner in which to purify proteins. Elution of the His-tagged protein takes place by displacing the bound His-tagged protein with imidazole. The greatest disadvantage of IMAC is that chelating agents need to be avoided as this will strip the support of metal ions (31).

β-Gal Characterisation

Characterisation of the β-gal enzymes showed that the E537D mutant β-gal had an activity that was 115× slower than the wildtype β-gal and that both enzymes have an affinity for lactose as a substrate. It was therefore decided to proceed with the immobilisation of β-gal (wildtype and mutant) on MNPs for the removal of lactose from solution.

Adsorption Behaviour of β-Gal on Functionalised Magnetic Nanoparticles

IMAC was used for the immobilisation of the His-tagged wildtype and E537D mutant β-gal on Dynabeads® from Invitrogen (His-tag Isolation and Pull Down (HIPD)). These superparamagnetic spherical particles have a uniform size and a consistent, defined surface for the adsorption or coupling of bioreactive molecules and contain an immobilised $Co^{2+}$ with two coordination sites available for interaction with the expressed His-tagged β-gal enzyme. Dynabeads® are typically 1 to 5 micrometers in diameter.

Characterisation of Immobilised β-Gal: Enzyme Activity and Lactose Binding

The ability of the immobilised E537D β-gal mutant to remove lactose from solution and hydrolyse a small fraction of the lactose to galactose and glucose to compensate for the loss of lactose was investigated, together with whether the immobilised wildtype β-gal displayed any apparent lactose binding (as it may hydrolyse lactose too rapidly).

The invention will now be described in more detail with reference to the following non-limiting examples.

EXAMPLES

Materials

FluidMAG-Q and fluidMAG-DXS MNPs were purchased from Chemicell GmbH (Germany). Qiagen plasmid midiprep kit was purchased from BDH Chemicals (UK). BgIII was purchased from Promega (South Africa). Amylose resin was purchased from New England Bio-labs (UK). HindIII, IPTG and DTT were purchased from Roche Diagnostics (South Africa). Kaleidoscope™ molecular weight marker was purchased from Bio-Rad (South Africa).

An Ultra Pure Milli-Q (MQ) water system was used for water in all experiments. The pTrcHis TOPO® TA expression kit and GeneTailor™ Site-Directed Mutagenesis system were purchased from Invitrogen (South Africa). ZR fungal/bacterial DNA kit™ and Zyppy™ Plasmid Miniprep kit were purchased from Inqababiotech (South Africa). All primers were purchased through Inqababiotech (South Africa) unless otherwise stated. Commercial β-Gal was purchased from Sigma (South Africa).

Imidazole (reagent grade >98%), Mercaptoethanol (>99%), Nickel (II) Sulphate hexahydrate, ONPG and Alkaline phosphotase coupled goat ant-rabbit IgG were purchased from Sigma (South Africa). HiTrap™ Chelating HP Column and ECL™ Western blot detection reagents were purchased from GE Healthcare, Amersham (South Africa). Lactose monohydrate was purchased from Merck (South Africa). Anti-β-galactosidase rabbit IgG was purchased from Invitrogen (South Africa) and HisProbe-HRP from Thermo Scientific (South Africa).

Dynabeads® (HIPD) were purchased from Invitrogen (South Africa). Ferrite magnet was purchased from Magnatech (South Africa). The Pierce BCA™ Protein assay kit was purchased from Thermo Scientific (South Africa).

$^{14}$C labelled lactose ($^{14}$C-1-glucose labelled lactose) and $^{14}$C glucose were purchased from Amersham (South Africa). A Carbohydrate Analysis column was purchased from Waters. Acetonitrile was purchased from Sigma (South Africa).

Bacterial strains and plasmids: The DNA template was provided in the *E. coli* strain MG1655 (courtesy Dr James Lloyd, Institute for Plant Biotechnology, Stellenbosch University). The pTrcHis TOPO® cloning vector (Invitrogen) was transformed into TOP10 cells (Invitrogen) for the original cloning. Site-directed mutagenesis products where transformed into DH5α™-T1$^R$ *E. coli* cells.

Methods

1. Removal of Maltose from Solution with Maltose Binding Protein Functionalised Magnetic Nanoparticles 1.1 Expression of MBP in *E. coli*

A 100× dilution of freezer stock was grown overnight with shaking (300 rpm) and 37° C. The overnight culture was diluted 100× and incubated at 37° C. (250 rpm) until an O.D$_{600}$ of 0.5 was reached. IPTG, to a final concentration of 3 mM, was subsequently added and the induced cells were incubated at 25° C. (225 rpm) for an additional 8 hours. Cells were separated from LB medium by centrifugation at 4000×g at 4° C. for 20 min. The supernatant was discarded and the pellet was resuspended in lysis buffer (20 mM TRIS-HCl, 200 mM NaCl, 1 mM DTT, 1 mM PMSF, 1 mM EDTA, pH 7.4) (10 ml per 1 g wet cell weight). Cell lysis occurred with pulsed sonication (Heat-systems Ultrasonic cell disrupter W-255r) at a 50% duty cycle (1 min per 10 ml lysis buffer) set at intensity of 4 followed by incubation at 4° C. for 30 min prior to centrifugation at 20000×g, 4° C. for 20 min. The soluble supernatant was stored at −20° C. for further purification.

1.2 Affinity Purification of MBP

The soluble expression supernatant was loaded onto a column packed with Amylose resin (10 ml) from Bio-Labs (UK) in Tris buffer (20 mM TRIS-HCl, 200 mM NaCl, 1 mM EDTA, 1 mM DTT, pH 7.4). The column was washed with 5× column volumes of Tris buffer. Elution took place with an elution buffer (10 mM Maltose, 20 mM TRIS-HCl, 200 mM NaCl, 1 mM EDTA, 1 mM DTT, pH 7.4) at a constant flow rate of 1 ml/min. The column effluent was monitored with a Bio-Rad Econo UV monitor recorded on an Amersham Biosciences recorder 112. Eluted fractions were monitored for protein at 280 nm. Analysis of the purified fractions was carried out by SDS-PAGE and Western blot analyses. MBP containing fractions were dialysed in dialysis buffer (20 mM TRIS-HCl, 20 mM NaCl, 1 mM EDTA, 1 mM DTT, pH 7.4). The dialysis buffer was changed twice a day over a period of 3 days. Dialysed fractions were freeze dried for three days and resuspended in 1 ml of analytical grade water.

1.3 Immobilisation of MBP on the MNPs

FluidMAG-Q and fluidMAG-DXS beads (0.2 mg) were incubated on ice for 30 min with 0.73 µg/µl MBP in a "positive buffer" (20 mM TRIS-HCl, 20 mM NaCl, 1 mM EDTA, pH 4) and a "negative" buffer (20 mM TRIS-HCl, 200 mM NaCl, 1 mM EDTA, pH 8.5) respectively. The beads were removed from suspension with the use of a magnet and the supernatant was removed for analysis. The beads were resuspended in the corresponding buffers and washed for an additional 30 min. The beads were then isolated with a magnet and the wash supernatant was removed for analysis. The supernatants as well as the MNPs with immobilised MBP were analysed by SDS-PAGE and protein determinations.

1.4 Removal of Maltose from Solution:

MNP functionalization: FluidMAG-Q and fluidMAG-DXS beads (0.2 mg) were incubated with a "positive buffer" (20 mM TRIS-HCl, 200 mM NaCl, 1 MM EDTA, 0.73 µg/µl MBP, pH 4) and a "negative buffer" (20 mM TRIS-HCl, 200 mM NaCl, 1 mM EDTA, 0.73 µg/µl MBP, pH 8.5) respectively. Incubation took place on ice for 30 min. The supernatant was removed for analysis and a washing step with the respective positive or negative buffers occurred for 30 min. The wash supernatant was removed. Protein concentration was determined of the supernatants with the BCA™ Protein Assay Kit. The fluidMAG-MBP MNP complexes were used in the maltose binding assay.

Maltose binding assay: Maltose solutions (100 µl, 15 mM and 20 mM respectively) were incubated on both the MBP functionalised MNPs (0.2 mg) for 1 hr. The supernatant was removed and a wash step took place in the corresponding positive and negative buffers for 30 min. The supernatants and wash steps were analysed by using a modified quantitative Benedict's test.

2. Cloning and Site Directed Mutagenesis of His-Tagged *Escherichia coli* β-Galactosidase 2.1. Cloning of the LacZ Gene 2.1.1. Genomic DNA Isolation

*E. coli* strain MG1655 genomic DNA was isolated using the ZR Fungal/Bacterial DNA kit™ MG1655 cells were grown in LB medium containing 0.1 mg/ml streptomycin. Cells were harvested by centrifugation and used in the ZR Fungal/Bacterial DNA kit™. The protocol was followed according to the manufacturer's specifications. DNA purity was analysed with a Beckman Coulter UV spectrophotometer at 260 and 280 nm.

2.1.2. Preparation of Insert DNA

Genomic DNA containing the lacZ gene from the *E. coli* strain MG1655 was used as a template for the preparation of the insert. A restriction site in the COOH terminus, that was compatible with BamH1, was incorporated with PCR.

2.1.3. Polymerase Chain Reaction

A PCR was performed with a Thermo Hybrid PCR Sprint thermocycler according to the protocol summarised in Table 2. lacZ amplification was performed with the polymerase PfuI by initial denaturation at 95° C. (1 min), followed by a second denaturation step at 95° C. for 30 s, which was followed by an annealing step at 58° C. for 30 s. The subsequent elongation lasted 8 min at 72° C. for 25 cycles. The resultant PCR product was stored at −20° C. DNA sequence analysis and agarose gel analysis were used to characterise the PCR product.

```
Left Primer: LacZ_LP
Sequence: 5'-GTCATGACCATGATTACGGATTCAC-3' (SEQ ID NO: 1)
Length: 25 Bp, % GC: 44, Tm: 62.94° C.

Right Primer: LacZ_RP
Sequence: 5'-CTGCCCGGATCCTATTATTTTTGACACCAGACCA-3' (SEQ ID NO: 2)
Length: 34 Bp, % GC: 47, Tm: 69.492° C.
```

TABLE 2

PCR protocol for amplification of LacZ gene from MG1655 *E. coli*

| PCR Mixture | Volume (μl) PCR Reaction | Volume (μl) Negative Control | Final Concentration |
|---|---|---|---|
| Milli-Q dH20 | 31.6 | 39 | |
| 10x PCR Buffer | 5 | 5 | 1x |
| dNTPs | 2 | 2 | 200 μM |
| Left Primer | 1.5 | 1.5 | 3 μM |
| Right Primer | 1.5 | 1.5 | 3 μM |
| Pfu DNA polymerase | 1 | 1 | |
| Template DNA | 7.4 | 0 | |
| Total | 50 | 50 | |

2.1.4. Addition of A-Overhangs

The PCR product was incubated with 1 unit Taq polymerase at 72° C. for 15 min. The taq polymerase provided the necessary A-overhangs in order to complete the cloning reaction. The product was stored at 4° C. overnight for use in the cloning reaction.

2.1.5. Cloning Reaction

A pTrcHis TOPO® TA expression kit (Invitrogen) was used in accordance with the manufacturers specifications. A cloning reaction (Table 3) was prepared and mixed gently at room temperature for 5 min.

TABLE 3

Cloning reaction mixture

| Reagent | Volume (μl) |
|---|---|
| Fresh PCR product | 1 |
| Sterile Water | 3 |
| TOPO Vector | 1 |
| Total | 5 |

2.1.6. Transformation Reaction

TOPO® cloning reaction mixture (1 μl) was added to one vial of One Shot® cells, mixed gently and incubated on ice for 30 min. Cells where heat shocked at 42° C. for 30 s without shaking after which the cells where immediately transferred to ice. SOC medium (250 μl, 25° C.) was added and the mixture was shaken horizontally at 37° C. for 30 min. The transformation mixture (50 μl) was plated onto an LB-Agar plate containing AMP (50 μg/ml, 0.5% glucose) and incubated overnight at 37° C.

2.1.7. Selection of Colonies

Ten single colonies were selected. TOPO10 *E. coli* cells, transformed with the pTrcHis-lacZ vector, were inoculated in 10 ml LB medium containing 50 μg/ml AMP and 0.5% Glucose at 37° C. The culture was incubated overnight (225 rpm). Cultures were labelled and kept for plasmid DNA preparation.

2.1.8. Plasmid DNA Isolation

The Zyppy™ plasmid mini-prep kit was used according to the manufacturers' protocol. The resulting plasmid DNA was stored at −20° C. for restriction enzyme digestion and sequencing. DNA purity was verified by the determining the absorbance ratio at 260 and 280 nm with a Beckman Coulter spectrophotometer.

2.1.9. Restriction Enzyme Digestion

To verify the transformation of the lacZ gene into the vector restriction enzyme (RE) digestions were utilised. EcoRI (Promega) and HindIII (Roche) were, separately, incubated with plasmid DNA for 2 hr at 37° C. according to the protocol summarised in Table 4. The RE digestion product was stored at −20° C. for agarose gel analysis.

TABLE 4

Restriction enzyme digestion mixture

| Reagent | Volume (μl) EcoRI | Volume (μl) BamHI |
|---|---|---|
| Restriction Enzyme | 1 | 1 |
| Milli-Q dH20 | 10.8 | 11 |
| Buffer | 2 | 2 |
| BSA | 0.2 | 0 |
| Plasmid DNA | 6 | 6 |
| Total | 20 | 20 |

2.2. Site Directed Mutagenesis of the LacZ Gene

A GeneTailor™ Site-Directed Mutagenesis System was purchased from Invitrogen and was used in accordance to the manufacturer's protocol.

2.2.1. Methylation Reaction

A fresh dilution of 10×SAM was prepared prior to the methylation reaction. The reagents listed in Table 5 were combined for 1 hr at 37° C. The methylation reaction mixture was stored at −20° C. prior to the mutagenesis reaction.

TABLE 5

Methylation reaction

| Reagent | Volume (μl) |
|---|---|
| Plasmid DNA | 0.61 |
| Methylation Buffer | 1.6 |
| 10x SAM | 1.6 |
| DNA Methylase | 1 |
| Milli-Q dH2O | 11.19 |
| Total | 16 |

2.2.2. Mutagenesis Reaction

Oligonucleuotide primers with the Glu-537 codon replaced by GAC were used. The primers are detailed below. Platinum Taq high fidelity polymerase was used for the amplification of the plasmid. Mutagenesis reaction reagents are detailed in Table 6. Amplification was obtained by initial denaturation at 94° C. for 2 min. A second denaturation step was performed at 94° C. for 30 s. Thereafter an annealing step was performed at 55° C. for 30 s and an elongation step at 68° C. for 8 min. This was allowed to cycle 20 times before a final 10 min incubation at 68° C. The mutagenesis reaction mixture was stored at 4° C. and kept for agarose gel analysis as well as the transformation reaction.

```
Left Primer: LacZ_MutLP
Sequence: 5'-CGCGCCCGCTGATCCTTTGCGACTACGCCCACGC-3' (SEQ ID NO: 3)
Length: 34 Bp, % GC: 71, Tm: 79.14

Right Primer: LacZ_MutRP
Sequence: 5'-TCGCAAAGGATCAGCGGGCGCGTCTCTCCA-3' (SEQ ID NO: 4)
Length: 30 Bp, % GC, 63.33, Tm: 74.2
```

TABLE 6

Amplification of mutated LacZ gene

| Component | Volume (μl) | Final Concentration |
|---|---|---|
| 10X High fidelity PCR Buffer | 5 | 1X |
| 10 mM dNTPs | 1.5 | 0.3 mM each |
| 50 mM MgSO$_4$ | 1 | 1 mM |
| Primers (10 μM each) | 1.5 | 0.3 μM each |
| Methylated DNA | 2 | |
| Platinum Taq High Fidelity (5 U/μl) | 0.2 | $2 \times 10^{-3}$ U/μl |
| Milli-Q dH20 | 37.3 | |
| Total | 50 | |

2.2.3. Transformation Reaction

DH5α™-T1® cells were thawed for 5 min before the addition of the mutagenesis reaction mixture (2 μl) and the resulting mixture was incubated on ice for 10 min. Cells were heat shocked at 42° C. for 30 s and subsequently placed on ice for 1 min. After heat shock treatment, the cells were shaken (225 rpm) horizontally at 37° C. for 1 hr. Transformation reaction mixture (125 μl) was plated onto LB-Agar plates containing 50 μg/ml AMP. The plates were inverted and incubated at 37° C. for 16 hrs. Colonies were selected and plasmid DNA isolation took place with a Zyppy™ plasmid mini-prep kit as previously described. Plasmid analysis was carried out using agarose gel electrophoresis and sequencing.

2.3. Analysis

2.3.1. Agarose Gel Electrophoresis Analysis

All PCR products and RE digests were analysed by agarose gel electrophoresis (1% agarose gel in TAE buffer with Ficoll orange as a loading dye). Agarose gels were visualised with the use of CyberGold (Invitrogen).

2.3.2. DNA Sequence Analysis

Nucleotide sequence information was determined using an Applied Biosystem's 3730xl DNA Analyser from the Central Analytical Facility at the University of Stellenbosch. The primer sequences used are listed in Table 7. Xpress™ forward and pTrcHis Reverse primers were supplied in the pTrcHis TOPO® TA expression kit.

TABLE 7

Primers used for DNA sequencing

| Primer Name | Primer Specificity | Primer Sequence |
|---|---|---|
| Xpress ™ Forward | Xpress ™ Forward Priming Site | 5'-TATGGCTAGCATGACTGGT-3' (SEQ ID NO: 5) |
| pTrcHis Reverse | pTrcHis Reverse Priming Site | 5'-GATTTATCTGTATCAGG-3' (SEQ ID NO: 6) |
| LacZ_MutLP LacZ_MutRP | Given previously | |

2.4 Protein Expression

LB medium (5 ml) was inoculated with wildtype and E537D mutant *E. coli* strains (50 µl freezer stock) in separate tubes and incubated overnight in a shaking incubator (225 rpm) at 37° C. The overnight cultures were diluted 50× into 100 ml fresh LB medium and grown to an $O.D_{600}$ of 0.5. The two cultures were then induced with IPTG (300 mM final concentration) and grown for a further 6 hours in a shaking incubator (225 rpm) at 37° C. The cells were harvested by centrifugation at 4000×g for 20 min at 4° C., resuspended in lysis buffer (20 mM TRIS-HCl, 100 mM NaCl, 1 mM DTT, 1 mM PMSF, 1 mM EDTA, 2% NP40, pH 7.4) and lysed by pulsed sonication at a 50% duty cycle. Protein was collected by centrifugation at 20000×g for 20 min at 4° C. The pellet was resuspended in lysis buffer and the soluble supernatants, containing protein, were both stored at −20° C. for further purification and SDS-PAGE and Western blot analyses.

2.5 Protein Purification

Immobilised metal affinity chromatography was performed with the use of an Amersham Biosciences ÄKTAprime protein chromatograph equipped with a HiTrap™ Chelating HP Column for both the wildtype and E537D mutant enzymes. Separate columns were used to avoid contamination between the two enzymes. The column was washed with three column volumes of MQ water and charged with a $NiSO_4$ solution (0.1 M). The excess nickel was removed using a wash buffer (500 mM $NaPO_4$, 300 mM NaCl, 20 mM Imizadole, 5 mM sodium metabisulphate, 20 mM β-mercaptoethanol, 10% glycerol, pH 8). The supernatant containing the expressed His-tagged protein was loaded onto the column and the column was washed with 10× column volumes to remove all non-specific proteins. An elution buffer (500 mM $NaPO_4$, 300 mM NaCl, 500 mM Imizadole, 5 mM sodium metabisulphate, 20 mM β-mercaptoethanol, 10% glycerol, pH 8) was subsequently applied to the column initially at 15% for 15 min and followed by an increase to 100% until β-gal eluted. Fractions (4 ml each) were collected into test tubes containing 1 ml MQ water and 0.2% tween20. Detection of eluting proteins occurred at 280 nm. The purified samples were subsequently dialysed for 48 hr against dialysis buffer (500 mM $NaPO_4$, 300 mM NaCl, 5 mM sodium metabisulphate, 0.2% tween20, pH 8) with a buffer change every three hours.

2.6 ONPG Activity Assay

Purified β-gal was assayed using a colorimetric activity assay. Both enzymes were assayed at varying substrate concentrations. The assay took place in phosphate buffer (93 mM Sodium phosphate, 1 mM $MgCl_2$, 112 mM β-mercaptoethanol, pH 7.3) with varying amounts of substrate concentration. The assay was performed in a BioTek® PowerWave 340 spectrophotometer at 37° C. for 5 min with a reading taken every 5 s. The buffers were preincubated at 37° C. for 30 min prior to the assay.

2.7 Competitive Activity Assay

The protocol for the above activity assay was repeated, but with the addition of lactose as an inhibitor. Lactose was added to final concentration of 6, 16 and 60 mM respectively.

2.8 Protein Analyses

Analyses of the expressed proteins were carried out using SDS-PAGE and Western blot analysis as previously described. A His-probe conjugated to HRP as well as anti-β-gal antibodies raised in a rabbit were used. For the secondary antibody, goat anti-rabbit antibodies conjugated to alkaline phosphotase were used.

3. Adsorption Behaviour of β-Gal on Functionalised Magnetic Nanoparticles 3.1 BCA Protein Determination To determine the amount (µg) of β-gal that was bound to Dynabeads® (HIPD), a BCA protein assay was performed according to the manufacturer's protocol. A standard curve with BSA was established in a range from 0 to 2 mg/ml. The analysis was performed at 540 nm.

3.2 Adsorption of β-Gal onto Dynabeads® (HIPD)

According to the manufacturer's specifications, 25 µl of the beads had a mass of 1 mg. A dilution series of purified β-gal wildtype and E537D mutant was prepared in a concentration range from 0 to 0.4 mg/ml. The dilution series was incubated with the beads (25 µl) for 10 min at 25° C. according to the manufacturer's protocol to ensure optimal adsorption of β-gal onto the beads. The beads were subsequently separated from the solution with a magnet and the supernatant was removed and analysed as described immediately above. The beads were then washed three times in dialysis buffer and the supernatant of the wash steps were also analysed for protein content.

3.3 The Effect of Temperature on Adsorption

The experimental procedure described above was repeated at 4 and 37° C.

3.4 The Effect of Time on Adsorption

Purified β-gal (wildtype and E537D mutant), was incubated with the beads (25 µl) at room temperature and optimal concentration to ensure maximum binding. The supernatant was removed from the solution at regular time intervals for 10 min. The collected fractions were assayed for protein content as described above. Analysis of β-gal bound to the beads took place with SDS-PAGE and Western blot analyses as outlined above.

4 Characterisation of Immobilised β-Gal: Enzyme Activity and Lactose Binding 4.1 Immobilisation of β-Gal onto Dynabeads (HTIP)

70 µg β-gal (both E537D mutant and wildtype) were incubated for 10 min at 25° C. on a Vortex Genie 2 mixer (Healthcare technologies, South Africa) with 25 µl Dyanbeads® (HIPD). The immobilised β-gal was collected with the use of a magnet and the residual supernatant was removed for protein analysis. The beads were then washed three times and the wash supernatant was also kept and analysed for protein content.

4.2 ONPG Activity Assay

The activity of the immobilized wildtype β-gal was determined with an ONPG activity assay as described earlier.

4.3 Radioactive Binding Assay

Immobilised β-gal (Wildtype and E537D mutant) (0.2 nmol β-gal/mg beads) was incubated with 0.2 nmol $^{14}C$ lactose in buffer (500 mM $NaPO_4$, 300 mM NaCl, 5 mM sodium metabisulphate, 0.2% tween20, pH 8) for 5 min. The immobilised β-gal was then removed from the $^{14}C$ lactose solution with a magnet. The original 0.2 nmol C14 solution and the residual supernatant from the binding experiment were analysed with a scintillation counter.

4.4 Partition HPLC

All HPLC analyses were carried out using a Carbohydrate Analysis column (Waters (WAT084038)) and a Radiomatic "Flo-one beta" A-100 radioactive flow detector at ambient temperature. An isochratic mixture of 20:80 water:acetonitrile was used as mobile phase at a flow rate of 2 ml/min. Scintillation fluid was pumped at 6 ml/min for radioactive detection. Retention times of $^{14}C$ glucose and $^{14}C$ lactose standards were determined separately. This was followed by analysis of the residual supernatant and original $^{14}C$ lactose solution from the lactose binding assay.

Results and Discussion

1. Removal of Maltose from Solution with Maltose Binding Protein Functionalised Magnetic Nanoparticles 1.1 Plasmid Isolation and Restriction Enzyme Digestion The plasmid pMalc2 needed to be present within the *E. coli* strain for expression of MBP. The pMalc2 plasmid (6646 bp) contains the MalE gene (839 bp) which encodes for MBP and has a single restriction site for both BglII and HindIII restriction enzymes.

Figure 2:
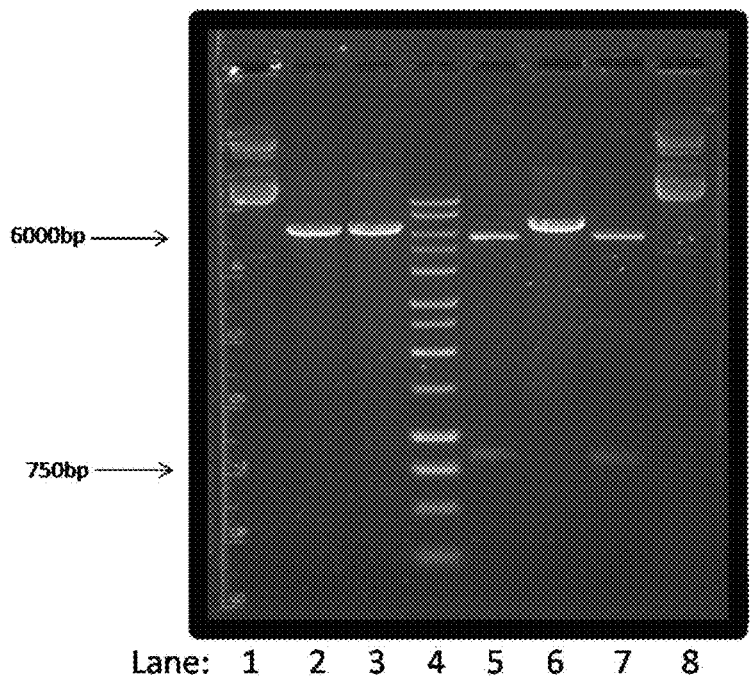
FIG. 2: 1.2% Agarose gel analysis in TAE buffer. Lane 1 and 9 contain undigested pMalc2 plasmid. Lane 2 contains a single restriction enzyme digest with BgIII. Lanes 3 and 6 contain a single restriction enzyme digest with HindIII. Lanes 5 and 7 contains a double restriction enzyme digest with both BgIII and HindIII to verify the presence of the pMalc2 plasmid. Lane 4 contains a 1 kb DNA ladder.

Restriction enzyme digestion with BglII and HindIII simultaneously, yielded two bands corresponding to 839 and 5810 bp respectively. The 839 bp fragment represents the MalE gene. The restriction enzyme digest confirmed that the pMalc2 plasmid was present. Single restriction enzyme digestion yielded a DNA fragment of 6646 bp long representing the pMalc2 plasmid DNA. This result can be seen in FIG. 2.

1.2 Protein Expression

Figure 3:
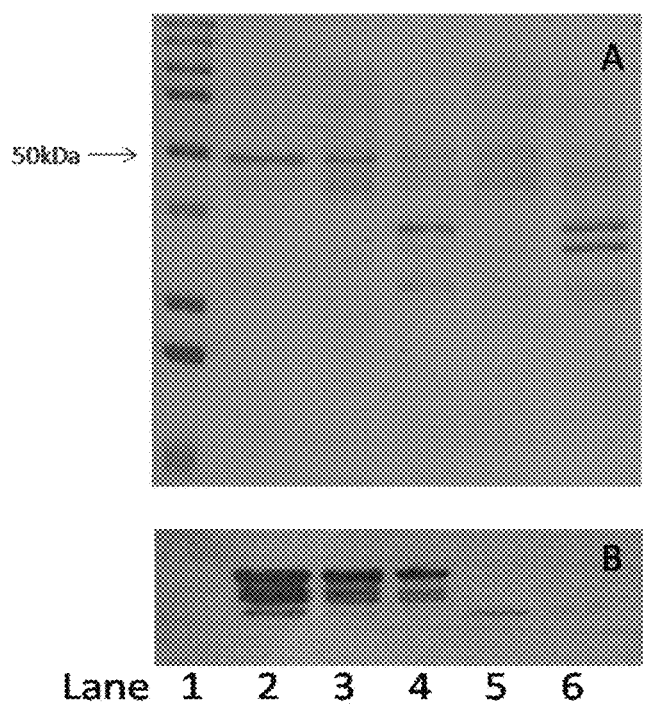
FIG. 3: SCS-PAGE gel (A) and Western blot (B) analysis representing expression of MBP, lane 1 contains a Kaleidoscope™ molecular weight marker. Lane 2 contains MBP. Lanes 3 and 4 contain the induced pellet and supernatant respectively. Lanes 5 and 6 contain un-induced supernatant and pellet respectively.

The cells were induced with IPTG for protein expression. Analysis with SDS-PAGE and Western blot analyses was conducted to determine protein expression and content. Analyses revealed that induction occurred and the supernatant contained MBP with a mass of approximately 42.5 kDa as stated in literature (36). The un-induced samples served as a control to determine whether IPTG induction occurred. From FIG. 3 it is apparent that induction occurred and protein, including MBP, was expressed. Western blot analyses confirmed that the band at 42.5 kDa corresponded to MBP.

1.3 Affinity Purification of MBP

Figure 4:
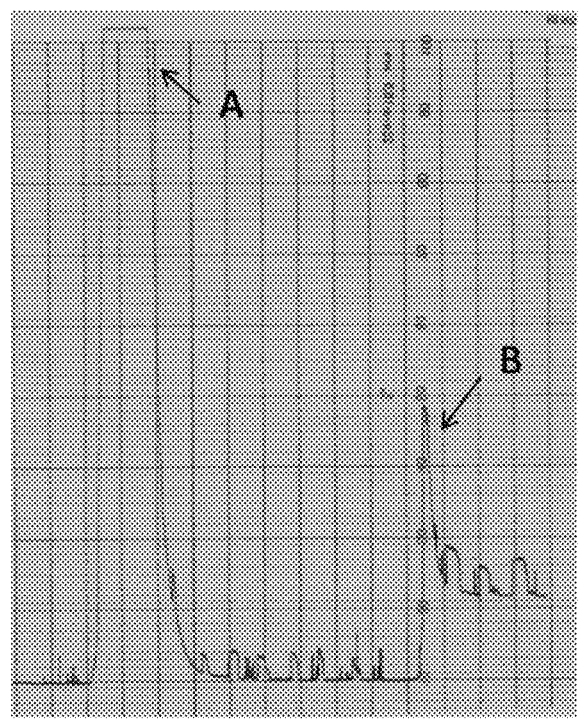
FIG. 4: Affinity chromatogram on an Amylose resin. Peak A represents the elution of the non-specific proteins and peak B represents the elution of MBP.
Figure 5:
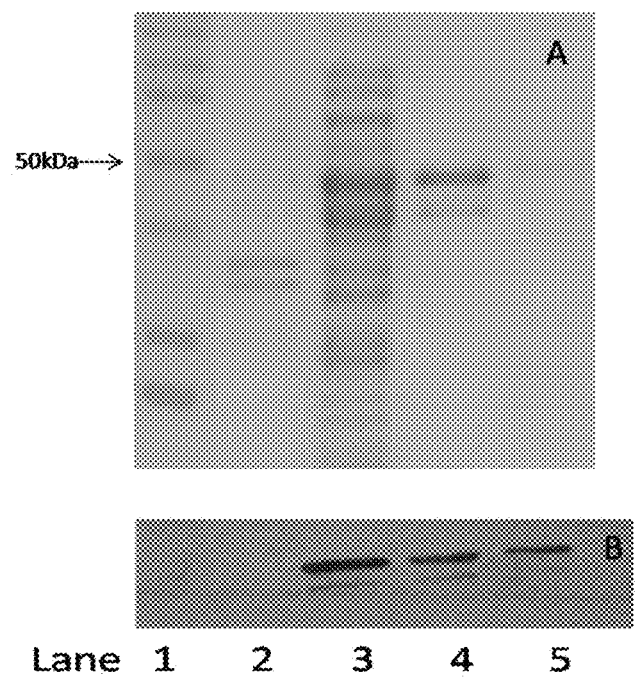
FIG. 5: Analysis of affinity chromatography purified fraction. A: SDS PAGE, B: Western blot. Lane 1 contains a Kaleidoscope™ molecular weight marker. Lanes 2 and 3 contain induced supernatant and pellet respectively. Lanes 4 and 5 contain purified fractions.

MBP has a high affinity for amylose and this provides an easy one step purification. Elution took place with maltose as MBP has a higher affinity for maltose than amylose. The purification chromatogram is shown in FIG. 4. The elution of MBP occurred over fractions 26 and 27, which is represented by peak B. Protein determinations were conducted with a Pierce BCA™ Protein assay kit. The concentrations were determined to be 0.734 µg/µl and 0.447 µg/µl for fraction 26 and 27 respectively. SDS-PAGE and Western blot analyses were performed in order to confirm that MBP was indeed present in fractions 26 and 27. This confirmation is shown in FIG. 5. Dialysis was performed on the fractions to remove the maltose. The MBP was concentrated by lyophilisation, but not to complete dryness. After freeze drying the protein concentrations of fractions 26 and 27 were 0.7305 µg/µl and 0.172 µg/µl respectively.

1.4 Immobilisation of MBP on the MNPs

Figure 6:
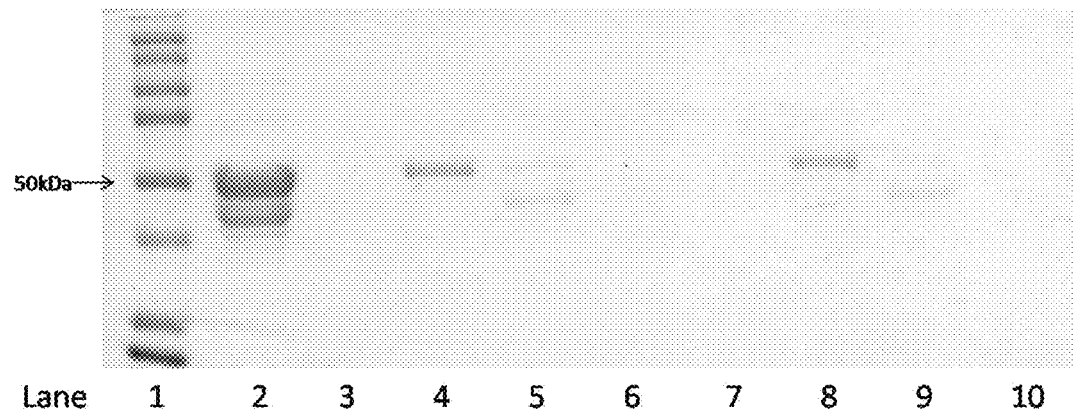
FIG. 6: SDS-PAGE analysis of MBP immobilisation on MNPs. Lane 1 contains a Kaleidoscope™ molecular weight marker. Lane 2 contains purified MBP. Lanes 3 and 7 contain the fluidMAG-Q and fluidMAG-DXS MNPs respectively. Lanes 4 and 8 contain fluidMAG-Q-MBP complex and fluidMAG-DXS-MBP complex respectively. Lanes 5 and 9 contain the solution out of which the MBP was immobilised for fluidMAG-Q-MBP and fluidMAG-DXS-MBP complexes respectively. Lanes 6 and 10 contain the wash steps for the fluidMAG-Q-MBP and fluidMAG-DXS complexes respectively.

It was important to determine whether MBP could be immobilised on the MNPs. As mentioned earlier, the net charge of proteins can be altered by changing the pH of the dissolving buffer to higher or lower than the pI of the protein. MBP has a pI of 5.1 and the buffers were set to have a pH of 4 and at pH 8.5 to induce a positive and negative charge respectively. It was then hypothesized that the positively charged fluidMAG-Q MNPs would have electrostatic interactions with the negatively charged MBP and vice versa. The MNPs were analysed without MBP to serve as a negative control and the SDS-PAGE results are shown in FIG. 6. The MNPs are too large to penetrate the SDS-PAGE gel as they have a molecular weight that far exceeds 250 kDa. During sample preparation for SDS-PAGE analysis any proteins present are denatured and hence the MBP immobilised on the MNPs will be released and migrate into the gel. This was observed for both the fluidMAG-Q-MBP and fluidMAG-DXS-MBP MNP complexes. The bands observed for wash steps in lanes 4 and 8 are significantly darker compared to those of lanes 5 and 9 indicating that there was more protein bound to the MNPs than there was left in the original solution. The amount of MBP bound was 120 µg MBP/mg fluidMAG-Q and 132.5 µg MBP/mg fluidMAG-DXS.

1.5 Removal of Maltose from Solution 1.5.1 Maltose Determination

Figure 7:
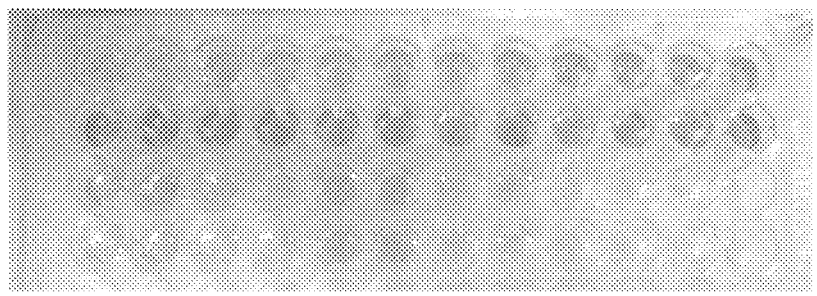
FIG. 7: Microtitre plate image of the quantitative Benedict's test for reducing sugars. Benedict's reagent changes from blue to an orange precipitate. Rows A and B represent the standard curve from 0 to 1 mM in 1 mM duplicate increments Rows C and D represent the maltose binding assay.
Figure 8:
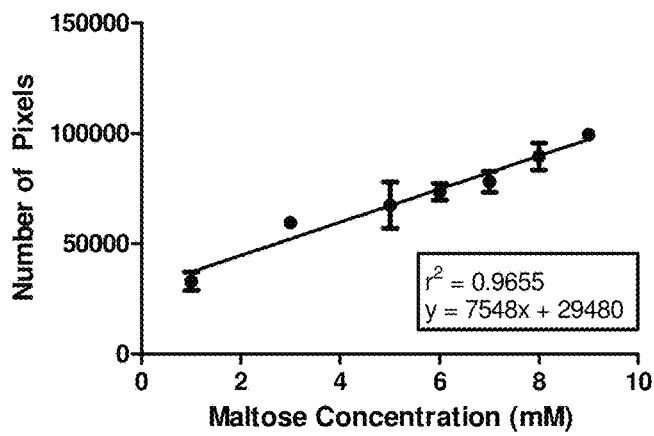
FIG. 8: Maltose standard curve created by the quantitative Benedict's test corresponding to rows A and B of FIG. 7 (n=3±SEM).

It was first necessary to establish a method to determine the concentration of maltose in an unknown solution. Since maltose is a reducing sugar, Benedict's reagent was chosen. Benedict's reagent is blue and reacts with a reducing sugar to create an orange precipitate. Due to the formation of a precipitate, the maltose concentration cannot be determined spectrophotometrically. In a micro titre plate, however, the amount of precipitate corresponds to the amount of reducing sugar present. It was determined that when the microtitre plate containing the maltose standard curve and samples was scanned onto a computer the image could be manipulated with the use of a software package called UN-SCAN-IT gel (Silk Software, Utah) version 6.1. The number of pixels per well could be determined and the pixel count correlated well with a specific maltose concentration. In FIG. 7 the first two wells were left blank whereas the wells that follow represent the standard curve (standards are in duplicate) from 1 to 10 mM Maltose in 1 mM increments (rows A and B). The standard curve (FIG. 8) was produced from the scanned image of the microtitre plate shown in FIG. 9 and analysed with UN-SCAN-IT gel.

1.5.2 Maltose Binding Assay

Figure 9:
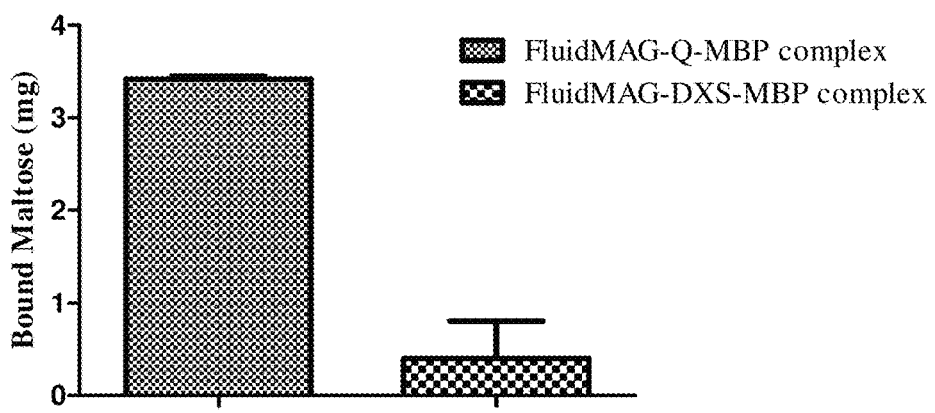
FIG. 9: Graph representing the concentration of maltose removed from solution using MBP ionically immobilised on the MNPs for both the fluidMAG-Q-MBP and fluidMAG-DXS-MBP complexes. The fluidMAG-Q-MBP complex was able to remove the most amount of maltose from solution, 3.4 mg maltose per 0.2 mg MBP functionalised MNPs.(n=3±SEM).

It was possible that, once the MBP was immobilised on the MNPs, it was no longer functional and thus could no longer bind maltose. This may have been due to MBPs active site or hinge region being blocked. Referring back to FIG. 7 rows C and D show the supernatants and wash step supernatants that were removed from the fluidMAG-Q-MBP MNP complexes during the maltose binding assay. The maltose concentrations used were 15 and 20 mM for both the fluidMAG-Q-MBP and fluidMAG-DXS-MBP MNP complexes. The results are shown in FIG. 9. It was also determined that the MNPs themselves do not bind the free maltose in solution.

The fluidMAG-Q-MBP MNPs bound approximately 3.4 mg maltose when 120 μg MBP was immobilised on 0.2 mg MNPs. It also revealed that the fluidMAG-DXS-MBP MNPs bound significantly less, approximately 0.8 mg maltose when 132.5 μg MBP is immobilised on 0.2 mg MNPs.

Figure 10:
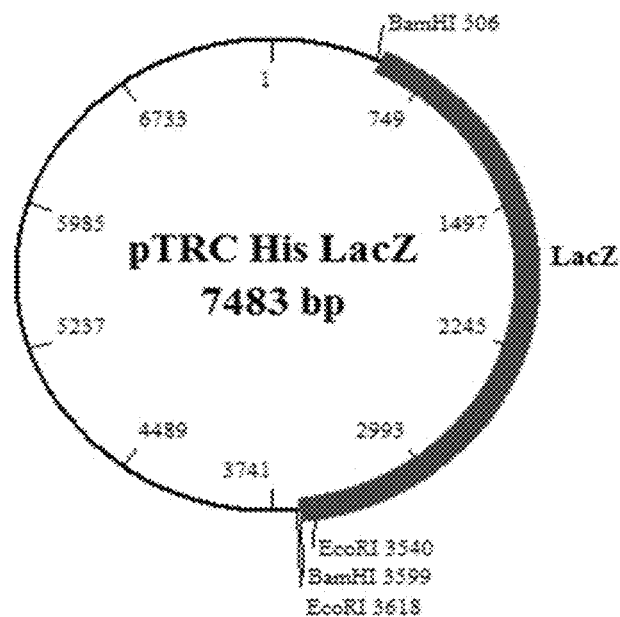
FIG. 10: Plasmid map of pTrcHis-lacZ showing the location of the lacZ gene (in red) as well as restriction sites for BamHI and EcoRI. BamHI was incorporated into the 3' end of the lacZ gene for RE digestion and colony selection.
Figure 11:
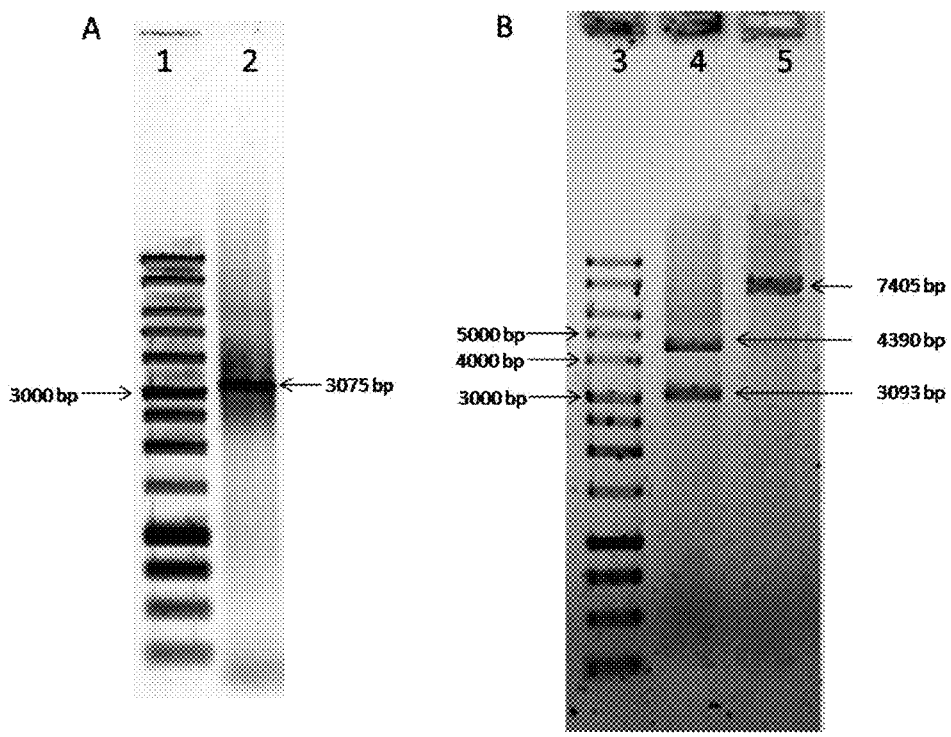
FIG. 11: Agarose gels showing the PCR amplification of the lacZ gene (A) and RE digestion of cloned product (B). Gel A; Lane 1: Promega 1 kB DNA marker. Lane 2: PCR amplified LacZ gene. Gel B; Lane 3: Promega 1 kB DNA marker, lane 4: BamHI digested pTrcHis-lacZ, Lane 5: EcoRI digested pTrcHis-lacZ.

2. Cloning and Site Directed Mutagenesis of His-Tagged *Escherichia coli* β-Galactosidase 2.1 Cloning of the LacZ Gene The lacZ gene was amplified from the genomic DNA of the MG1655 strain of *E. coli* with the use of PCR. A BamHI restriction site was incorporated into the 3' terminal (plasmid map shown in FIG. 10). The PCR product (50 μl) was analysed with the use of a 1% agarose gel in TAE buffer. The 3075 bp PCR product depicting the lacZ gene is illustrated in FIG. 11.

The pTrcHis vector is linearised and contains single thymidine (T) overhangs for TA cloning with topoisomerase I covalently bound. Taq polymerase adds A overhangs but is not a proof reading enzyme and has a mutation rate of approximately 1 bp per 1000 bp. Due to the large nature of the lacZ gene (3075 bp) a proof reading enzyme was utilized in the PCR step to ensure that no mutations occurred. Taq polymerase was initially used and at least three mutations were seen per PCR product. A difficulty arose because the proof reading enzyme did not provide the necessary A overhangs in order for the cloning to take place and an incubation step with Taq polymerase was added for this reason as recommended by the manufacturer.

In order to determine whether the transformation had taken place, plasmid isolation and subsequent RE digestion was performed. BamHI cut the pTrcHis_lacZ plasmid twice yielding two bands on the agarose gel, one corresponding to 4390 bp and the other corresponding to 3093 bp, as shown in FIG. 11. The pTrcHis-lacZ plasmid was also digested with EcoRI and revealed a 7405 bp band and a 78 bp band. The 78 bp band was too small to be detected on a 1% agarose gel. If the lacZ gene had not been inserted into the cloning vector the RE digest would have revealed a single band corresponding to 4390 bp.

The pTrcHis-lacZ plasmid was analysed with DNA sequencing. The results showed that the lacZ gene was inserted in the correct orientation and reading frame and that no mutations occurred (results not shown).

2.2 Site-Directed Mutagenesis

The PCR product of the mutagenesis reaction was analysed with an agarose gel. FIG. 12 shows the presence of the plasmid within the cells by a single band at 7483 bp. To determine whether the pTrcHis-lacZ plasmid contained the correct mutation and no others the lacZ gene was sequenced. The sequencing results revealed that site directed mutagenesis had taken place and a portion of the nucleotide sequence is given in FIG. 13 (SEQ ID NO: 7). The mutation is at position 2139.

2.3 Expression

Figure 14:
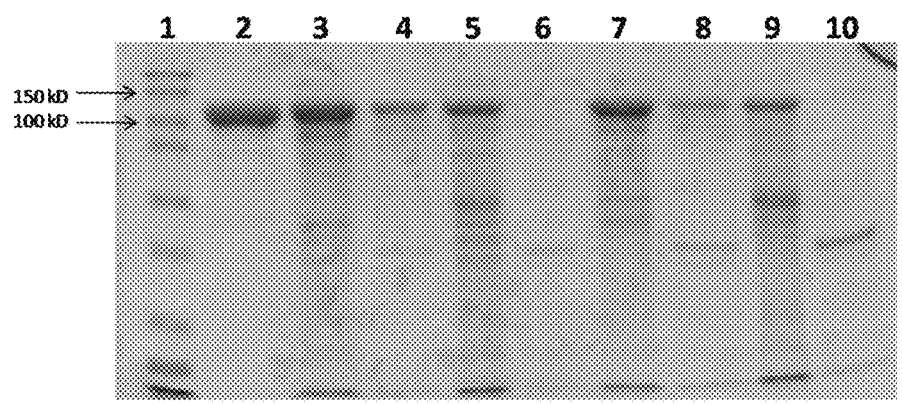
FIG. 14: SDS-PAGE gel of expressed wild type and E537D mutant β-gal. lane 1; Kaleidoscope™ molecular weight marker, lane 2; β-gal standard (Sigma), lane 3; Wildtype induced supernatant, lane 4; wildtype induced pellet, wildtype unindicted supernatant, lane 6; Wildtype un-induced pellet, lane 7; E537D mutant induced supernatant, lane 8; E537D mutant induced pellet, lane 9; E537D mutant un-induced supernatant, lane 10; E537D mutant un-induced pellet.

Protein expression was induced with IPTG and analysed with the use of SDS-PAGE and Western blot analyses. Uninduced cultures served as a control for protein expression. It is clear from the data presented in FIG. 14 that there is significantly less protein in the un-induced samples when compared to the induced samples. Beta-gal is a homotetramer of 464 kDa and when analysed on a SDS-PAGE gel should reveal a band corresponding to 116 kDa. The addition of the His-tag β-gal added 5 kDa to the molecular weight of both the wildtype and E537D mutant, yielding proteins with a molecular weight of approximately 120 kDa. This comparison can be seen in FIG. 14 (lanes 2 and 3). Lane 2 contains a commercially available β-gal from Sigma whereas lane 3 contains the wildtype β-gal. The band that correlates to β-gal in lane 3 is slightly higher than of the band in lane 2.

Figure 15:
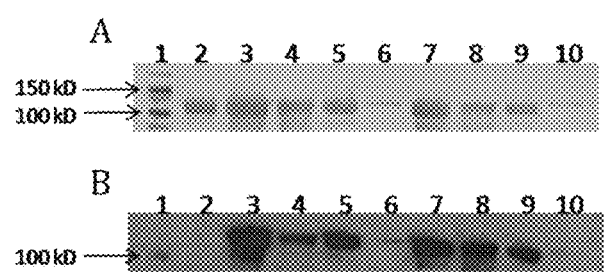
FIG. 15: Western blot analysis of expressed wild type and E537D mutant β-gal. A: Rabbit anti-β-gal antibodies with goat antirabbit alkaline phosphotase as a secondary antibody, B: HisProbe-HRP. The lanes correspond to that of the SDS-PAGE analysis in FIG. 14.

Western blot analysis (FIG. 15) was conducted with a HisProbe-HRP (A) as well as rabbit anti-β-gal antibodies with goat antirabbit alkaline phosphotase as a secondary antibody (B). Western blot analysis was performed in order to determine whether the band observed at a Mr corresponding to 120 kDa was indeed β-gal. It is possible to visualise the commercial β-gal in blot A since the antibodies are raised against β-gal. However it is not possible to detect the commercial β-gal in blot B as the commercial β-gal does not contain a His-tag. The Kaleidoscope™ molecular weight marker contains His-tagged proteins observed in blot B. The SDS-PAGE and Western blot analyses revealed that the cloning and site-directed mutagenesis from Chapter 5 was successful and the *E. coli* strains were able to express β-gal (both the wildtype and E537D mutant).

2.4 Protein Purification

Figure 16:
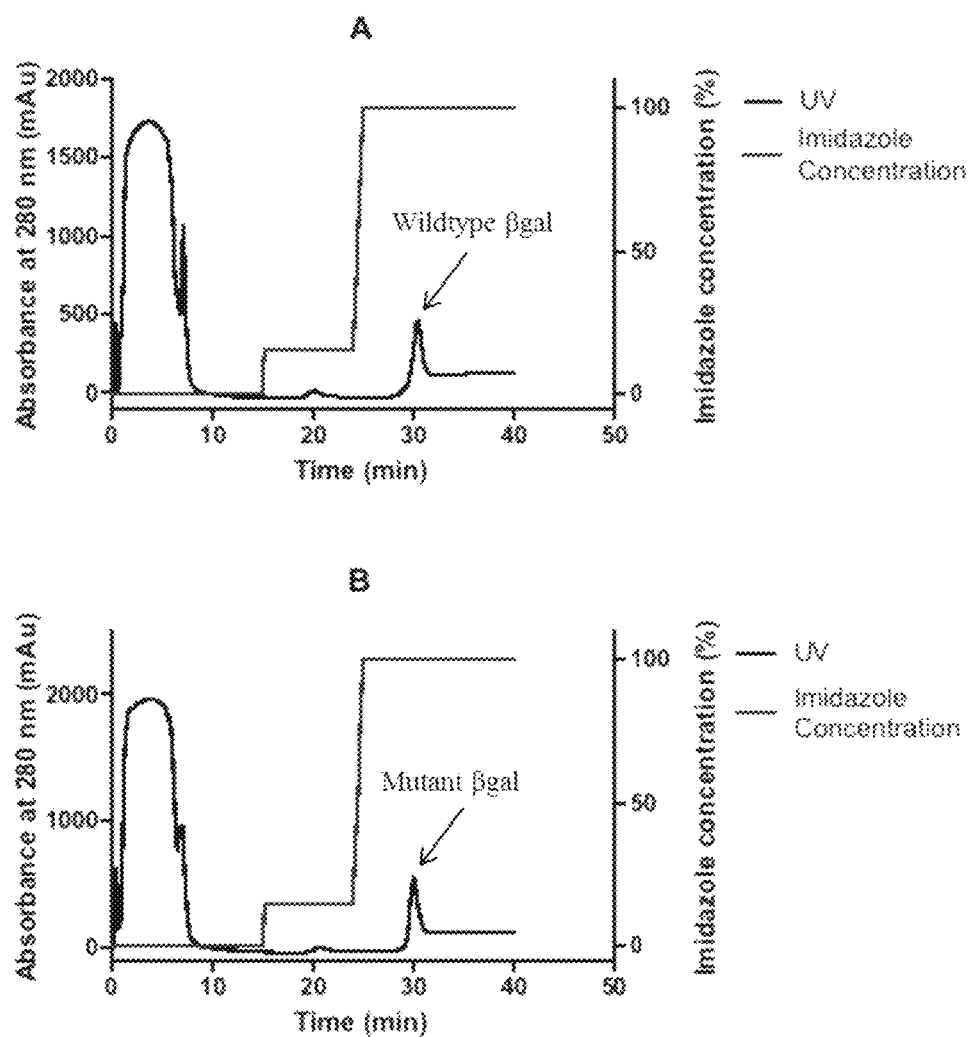
FIG. 16: Chromatograms showing IMA purification of β-gal. Chromatogram A represents the wildtype and chromatogram B represents the E537D mutant. The his gradient profile is the stepped line. The peaks indicated by the arrows are wildtype βgal (chromatogram A) and the mutant (chromatogram B).

IMAC provided a facile single step purification of β-gal. Once the non-specific proteins have been eluted the percentage of imidazole was increased in two increments. The initial increment (15%) eluted non-specific binding proteins with a high His content. The second increment (85%) allowed for the elution of the β-gal (FIG. 16). The first and most prominent peak represents the elution of further non-specific *E. coli* proteins, the smaller second peak represents the elution of non-specific His rich proteins and the third peak (indicated by the arrow) represents the elution of β-gal for both the wildtype (A) and the E537D mutant (B). As His-tagged proteins tend to aggregate, the tubes in which β-gal was collected contained tween20 and analytical grade water. The high molecular weight and high degree of purification of β-gal (relatively high concentration) also contributed to protein aggregation.

Figure 17:
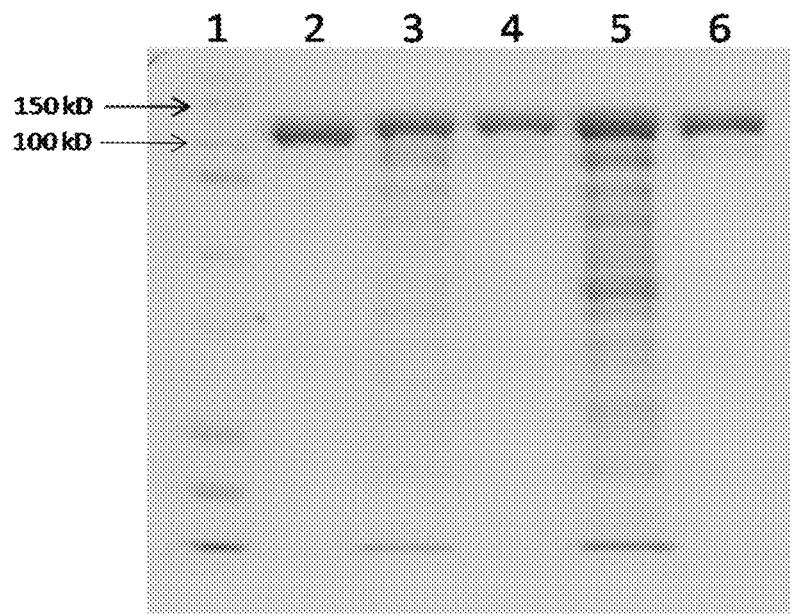
FIG. 17: SDS-PAGE gel representing IMA purification of wild type and the E537D mutant of β-gal. Lane 1; Kaleidoscope™ molecular weight marker, lane 2; β-gal standard (sigma), lane 3; Wildtype induced supernatant, lane 4; Wildtype purified fraction, lane 5; E537D mutant induced supernatant, lane 6; E537D mutant purified fraction.
Figure 18:
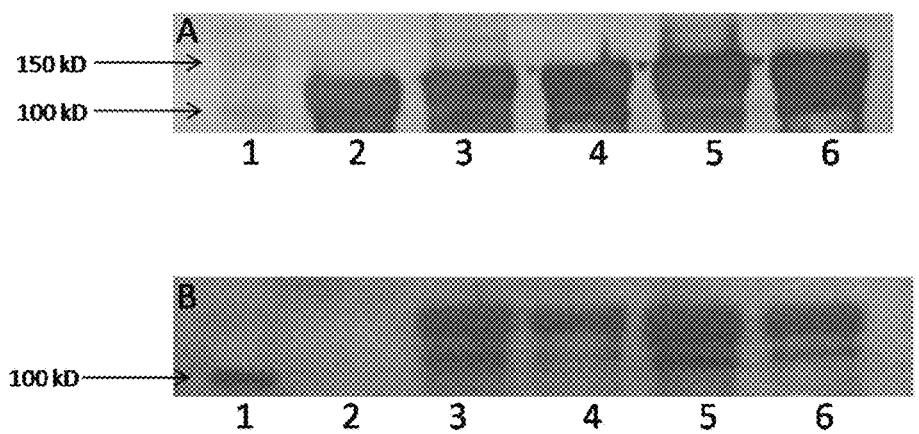
FIG. 18: Western blot analyses of wild type and the E537D mutant of β-gal. A: Rabbit anti-β-gal antibodies with goat antirabbit alkaline phosphotase as a secondary antibody, B: HisProbe-HRP. The lanes correspond to that of the SDS-PAGE analysis in FIG. 17.

The fractions in which the wildtype and E537D mutant were eluted were analysed by SDS-PAGE and Western blot analyses. These results showed that the purification of β-gal with IMAC was successful in a single step (FIGS. 17 and 18). The purified β-gal was subsequently dialysed to remove the imidazole, as it interferes with protein determinations and further downstream analyses. After dialysis the protein concentration of the wildtype was 0.98 mg/ml and the E537D mutant was 0.84 mg/ml.

2.5 ONPG Activity Assay

The activity of the E537D mutant was significantly lower than that of the wildtype according to Yuan et al (11). The activity needed to be determined for both the wildtype and E537D mutant β-gal prepared for this study, since the addition of the His-tag could influence enzyme activity. The activity of β-gal was determined using the ONPG activity assay. The kinetic parameters ($K_m$ and $V_{max}$) were determined using the Michaelis Menten equation and Graphpad Prism® version 5 software for Windows, Graphpad Software, La Jolla Calif. USA.

Figure 19:
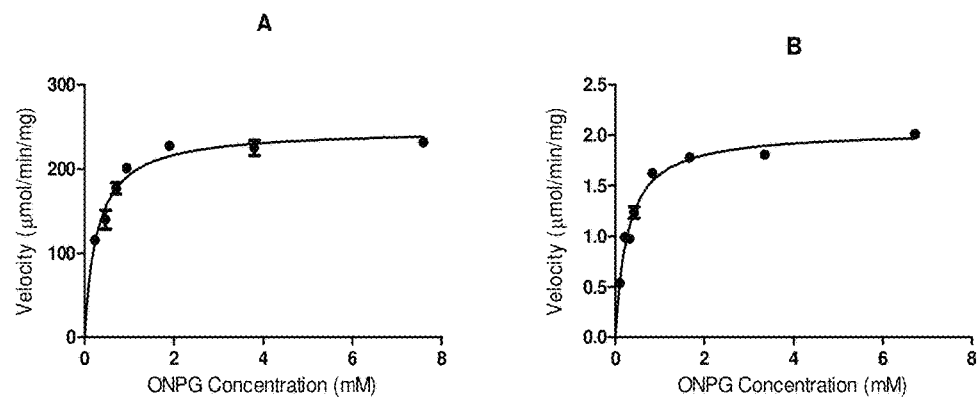
FIG. 19: Michaelis Menten Plots of β-gal ONPG activity. A represents the wildtype activity with a $K_m$ of 0.22 mM and a $V_{max}$ of 230 μmol/min/mg protein. B represents the E537D mutant with a $K_m$ of 0.27 mM and $V_{max}$ of 2 μmol/min/ protein.

The results of the enzyme activity determinations of the β-gal wildtype and the E537D mutant are shown in FIG. 19 (A and B). The $K_m$ determined for the wildtype was 0.22 mM and the $K_m$ for the E537D mutant was 0.27 mM using ONPG as substrate. These values do not differ significantly and indicate that the two forms of the enzyme (wild type and mutant) have the comparable affinities for ONPG. This finding was in agreement earlier reports in the literature (11). The $V_{max}$ values of the two enzymes, however, differed significantly. For the wildtype the $V_{max}$ was 230 μmol/min/mg protein and for the E537D mutant the $V_{max}$ was 2 μmol/min/mg protein. The E537D mutant has an activity that is 115× lower than the wildtype. Glu537 is responsible for the formation of an α-galactosidic bond with C1 of the β-D-galactoside. The replacement of a glu residue with an Asp will allow for the same bond formation but the carboxyl group of the Asp will be further away from the β-D-galactoside and hence lower the activity.

2.6 Competitive Activity Assay

The assay for the activity of β-gal, with lactose as substrate, is relatively complex and generally requires the use of HPLC. It was therefore decided to use a competitive activity assay instead. Lactose was therefore added together with ONPG to determine if the expressed enzymes did have an affinity for the natural substrate. Lactose would compete for the active site with ONPG and therefore the greater the inhibition the higher the affinity of lactose for that particular active site.

Figure 20:
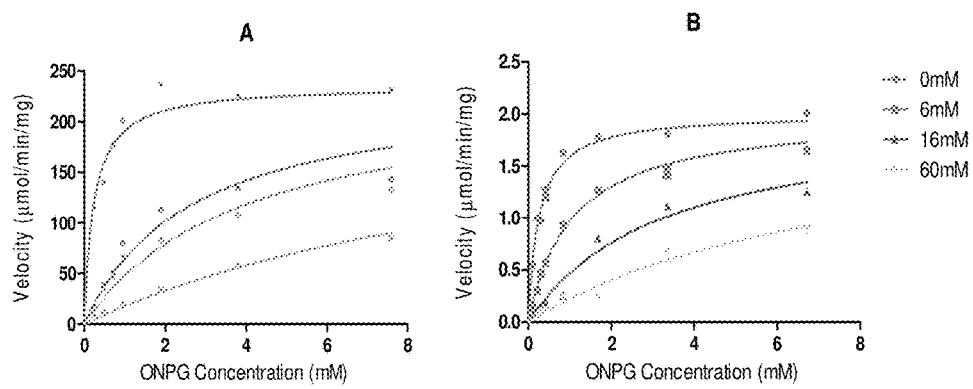
FIG. 20: Michaelis Menten plots of the competitive inhibition of the two βgal enzymes by lactose with ONPG as substrate. (A) represents the wildtype for which the $K_i$ was 12.4 mM and (B) represents the E537D mutant with a $K_i$ of 19 mM.

The results obtained were analysed with the aid of Michaelis Menten plots and the $K_i$ values for lactose were determined using Graphpad Prism® version 5 for Windows, Graphpad Software, La Jolla Calif. USA. The results are displayed in FIG. 20.

The $K_i$ for the E537D mutant was 19 mM whereas for the wildtype the $K_i$ was 12.4 mM, indicating a stronger inhibition of the wildtype by lactose. These results suggest that the wildtype enzyme has a somewhat larger affinity for lactose than the E537D mutant. The apparent difference in affinity for lactose and ONPG between the wildtype and the E537D mutant may be contributed to differences in structure between the two substrates. Since the inhibition was competitive the $V_{max}$ values remained the same as it was in the previous ONPG activity assay; 230 μmol/min/mg for the wildtype and 2 μmol/min/mg for the E537D mutant.

It is apparent from the above results that the inhibition exhibited by the addition of lactose to the ONPG solution is competitive as the $V_{max}$ remained unchanged whereas the $K_m$ was increased in response to lactose as a competitive inhibitor. The $K_m$ for the competitive inhibition cannot be directly compared to the $K_m$ of the ONPG activity assay but serves as an indirect means in which to analyse whether the enzymes display an ability to bind lactose.

3. Adsorption Behaviour of β-Gal on Functionalised Magnetic Nanoparticles

3.1 Standard Curve Construction

Figure 21:
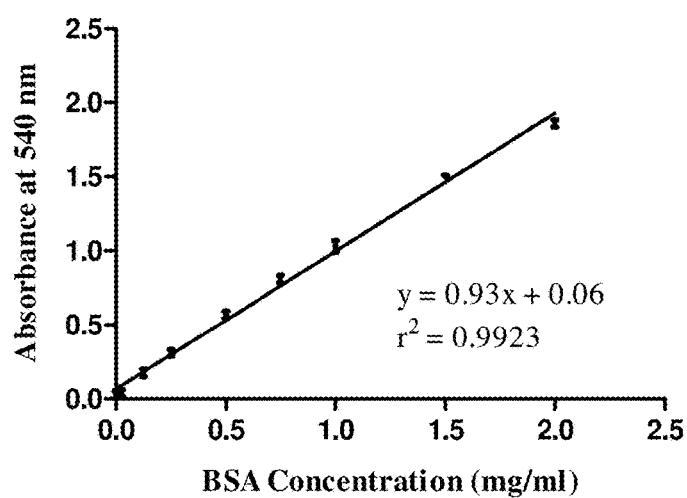
FIG. 21: Typical BSA standard curve obtained using the BCA® protein determination kit. The standard curve was determined according the BCA method of protein determination at 540 nm with the concentration of BSA standards ranging from 0 mg/ml to 2 mg/ml.

An accurate standard curve needed to be constructed in order to quantify the protein concentration in the binding experiments. The Peirce BCA protein determination kit was utilised with the use of BSA as a standard. The kit yielded a reproducible linear standard curve ($R^2$ values above 0.98) and for protein concentrations between 0 to 2 mg/ml. A typical standard curve is shown in FIG. 21 and the concentration of unknown protein samples could be accurately determined.

3.2 Adsorption of β-Gal onto Dynabeads® (HIPD)

His-tagged proteins have a tendency to aggregate and this was seen at high β-gal concentrations and in the absence of detergent. During purification β-gal was eluted into a Tween-20 solution, rather than EDTA which is routinely used, to avoid aggregation, since EDTA would have stripped the beads of the cobalt ions.

Figure 22:
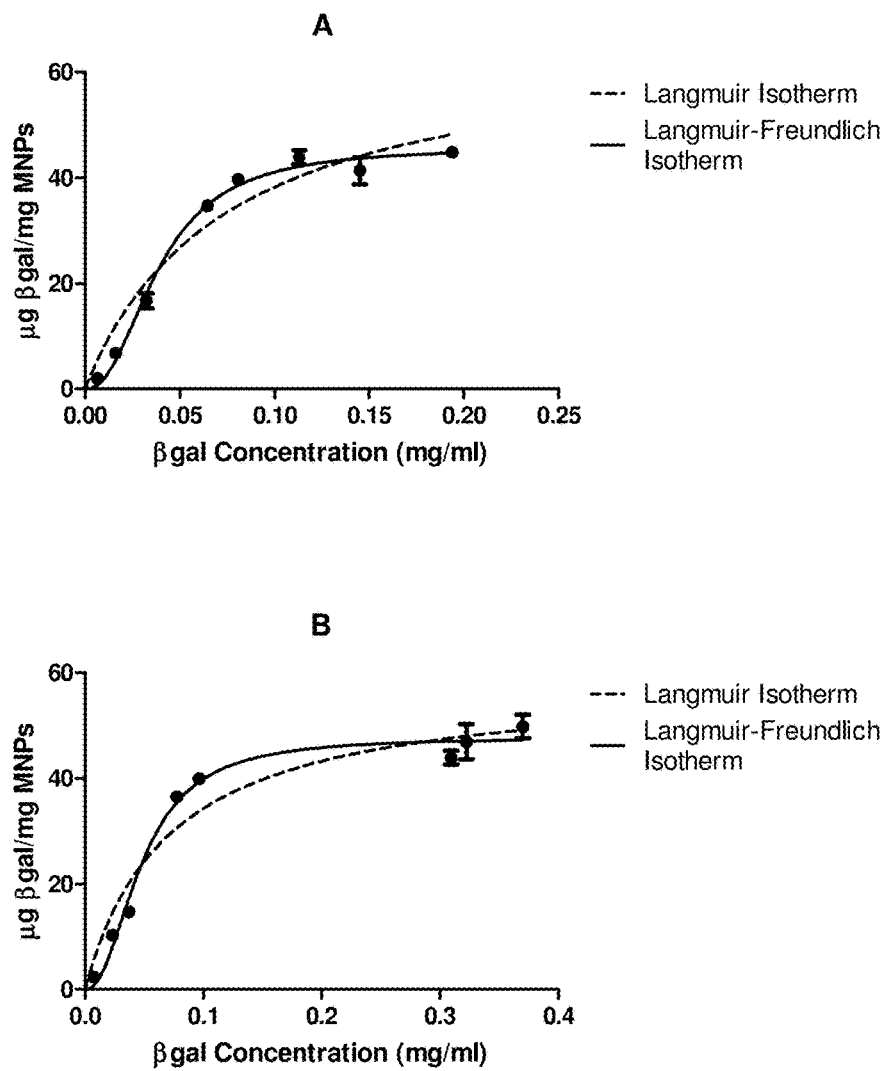
FIG. 22: Adsorption isotherms with both Langmuir (dotted line) and Langmuir-Freundlich models (solid line). The Langmuir-Freundlich isotherm was determined to represent the adsorption with better accuracy. A: Wildtype B: E537D Mutant. The maximal binding ($q_m$) was determined from the data.

The isotherms for both enzymes are shown in FIG. 22. The binding was initially analysed with the use of Langmuir isotherms and is shown as the dotted line in the figure. The $R^2$ values did not represent a satisfactory fit as it was 0.7 for the wildtype and 0.91 for the E537D mutant. The data was subsequently fitted to the Langmuir-Freundlich equation (shown by the solid line) which yielded $R^2$ values of 0.97 for both enzymes. Since the enzyme has a relatively high molecular weight the assumption for one binding site per one molecule, as outlined by the isotherm assumptions, may not hold true. From the data the Langmuir-Freundlich coefficient (n) was determined to be 2.29±0.241 for the wildtype and 2.21±0.246 for the E537D mutant. This indicates that the adsorption of β-gal to the beads exhibit positive cooperativity therefore the binding of one molecule promotes the binding of the other, possibly due to nonspecific protein-protein interaction on the surface of the beads. The $K_d$ was determined to be 0.34±0.0022 and 0.48±0.003 mM for the wildtype and E537D mutant respectively. The maximal binding ($q_m$) was determined from the data with the use of the Langmuir-Freundlich isotherm to be 45.88±1.422 μg β-gal per mg of beads for the wildtype and for the E537D mutant a value of 47.81±1.273 μg β-gal per mg of beads.

The relative small differences in n and maximum binding capacities between the β-gal wildtype and the E537D mutant was expected as the mutation was made in the active site and therefore not exposed to the beads where it could influence binding. Furthermore the his-tag on both enzymes was identical and in the same position for both enzymes. The manual from the bead manufacturer stated a 40 μg maximum binding capacity for a 28 kDa protein and the higher binding capacity obtained for β-gal, despite the larger molecular weight of β-gal, can be attributed to the positive cooperativity observed.

Figure 23:
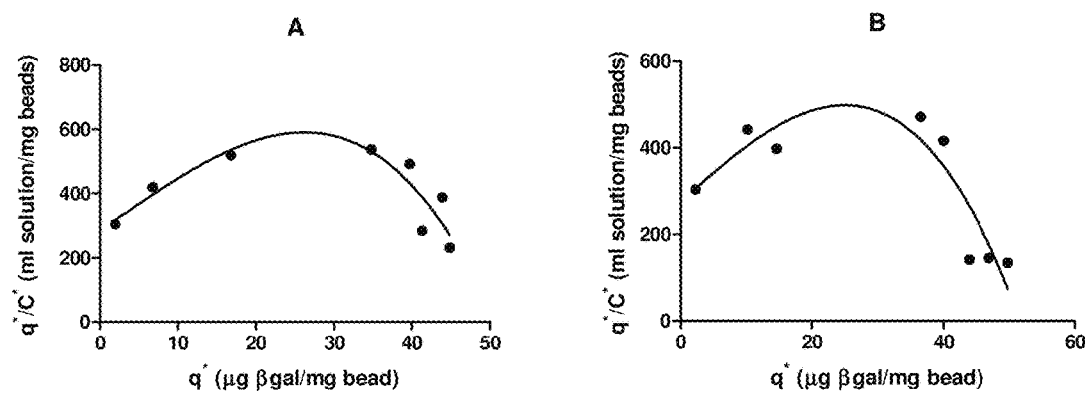
FIG. 23: Scatchard plots with the use of a Langmuir-Freundlich model. The downward curves indicate positive cooperitivty. A: Wildtype B: E537D mutant.

After the data for the isotherms was acquired it was transformed into Scatchard plots with the use of Graphpad Prism version 5 for Windows, Graphpad Software, La Jolla Calif. USA. The graphs are shown in FIG. 23. The Scatchard plots for both enzymes show a downward curve which is in agreement with the Langmuir-Freundlich coefficient that indicated the positive cooperativity.

3.3 Analysis of β-Gal Immobilisation

Figure 24:
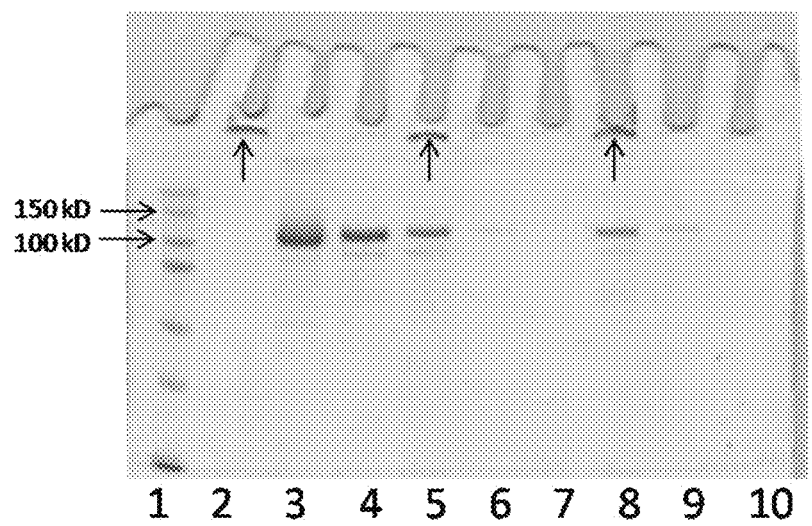
FIG. 24: SDS-PAGE gel for β-gal binding analysis. Lane 1: Kaleidoscope™ molecular weight marker. Lane 2: Naked beads. Lane 3: β-gal standard (Sigma). Lane 4: purified wildtype β-gal. Lane 5: Wildtype β-gal-bead complex. Lane 6: Remaining wildtype β-gal in solution after binding. Lane 7: Wash steps for wildtype β-gal-bead complex. Lane 8: E537D mutant β-gal-bead complex. Lane 9: Remaining E537D mutant β-gal in solution after binding. Lane 10: Wash steps for E537D mutant β-gal-bead complex. The arrows indicate the beads remaining in the loading wells.
Figure 25:
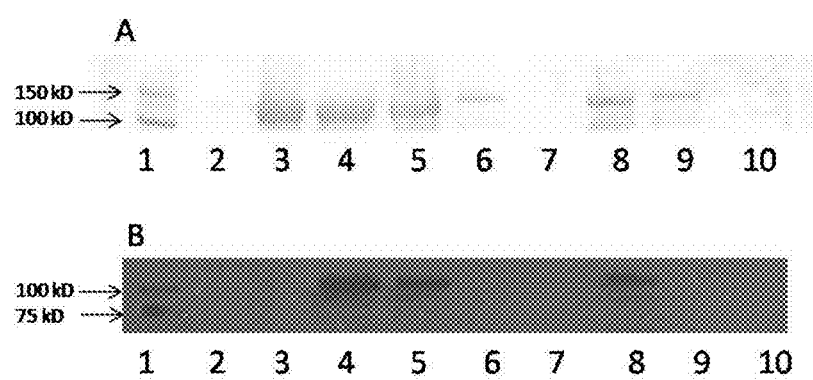
FIG. 25: Western blot analysis of β-gal binding analysis. Blot A: Rabbit anti-β-gal antibodies with goat antirabbit alkaline phosphotase as a secondary antibody B: HisProbe-HRP. The lanes correspond to that of the SDS-PAGE analysis in FIG. 24.

Direct analysis of the protein bound to the beads was achieved with SDS-PAGE and Western blot analysis. The images are shown in FIGS. 24 and 25. The naked beads were analysed to determine whether they had an effect on the procedure. The beads performed as expected and did not migrate during SDS-PAGE analysis since they are too large to penetrate the gel. This is indicated in lane 2 of FIG. 24 where only the naked beads were analysed as well as lanes 5 and 8 for the β-gal adsorption. The beads remained in the loading wells and are indicated by the arrows.

The β-gal-bead complex was treated by denaturation according to Låmmli and hence β-gal was no longer immobilised on the beads as can be seen in lanes 5 and 8. The β-gal was bound to the beads from a solution containing 70 μg β-gal and the remaining β-gal content was analysed to visualise the reduction. The remaining β-gal in the supernatant is reduced compared to the amount bound to the beads. The wash steps (lanes 7 and 10) revealed that virtually no β-gal is released even after three subsequent wash steps and that immobilisation was efficient. Western blot analyses were performed to validate the presence of the β-gal on the beads. The first blot (A) represents the presence of the His-tag and the second blot (B) represents the presence of β-gal protein.

3.4 Effect of Temperature on Adsorption

Figure 26:
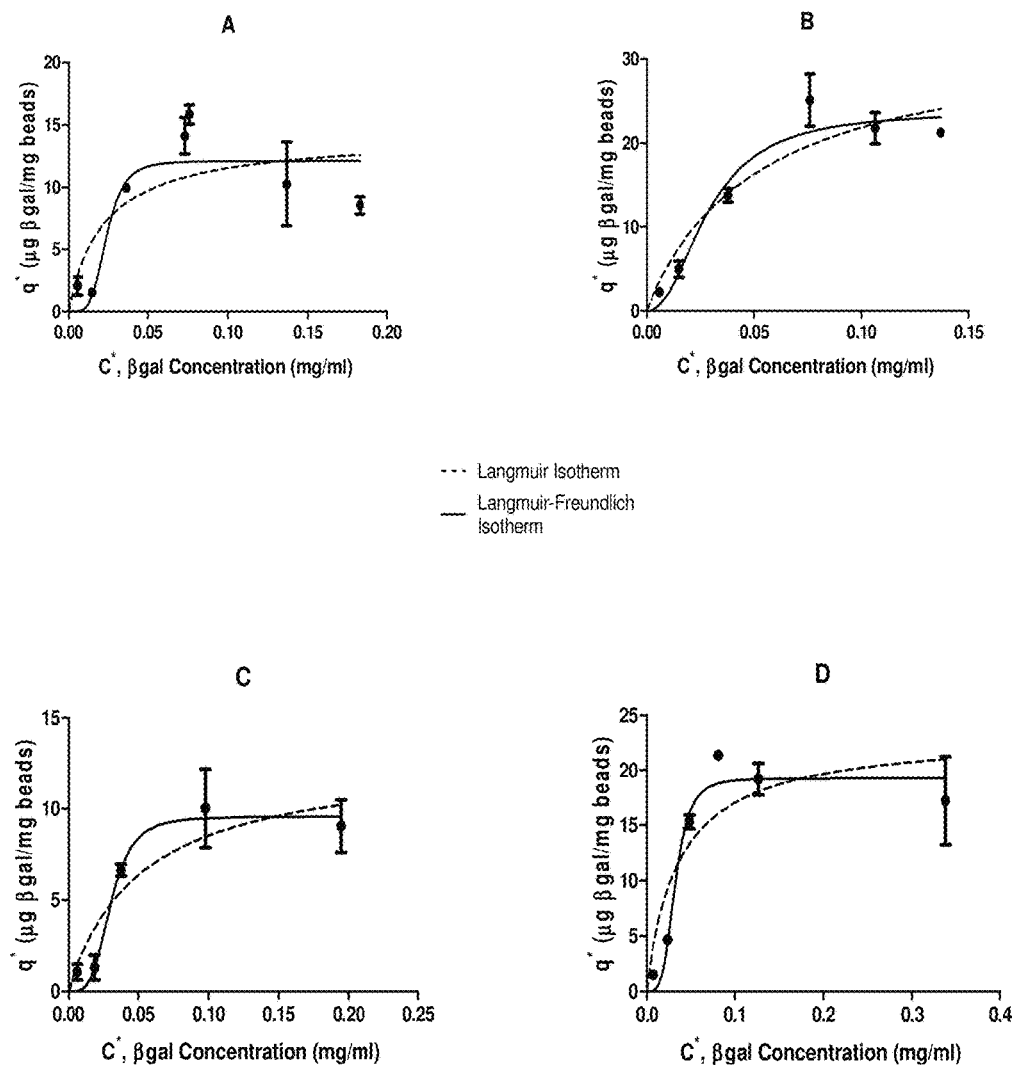
FIG. 26: Adsorption isotherms at differing temperatures analysed with Langmuir (dotted line) and Langmuir-Freundlich (solid line) isotherms. A: Wildtype at 37° C. B: Wildtype at 4° C. C: E537D mutant at 37° C. and D: E537D mutant and 4° C. The temperatures showed a reduced amount of β-gal bind.

The optimal temperature at which β-gal bound to the beads needed to be established. A temperature of 37° C. was chosen since this was the optimal temperature reported for maximum β-gal activity (10). A temperature of 4° C. was also chosen to determine whether lower temperatures affected protein binding to the beads. The results from these experiments can be seen in the adsorption isotherms in FIG. 26. The binding of β-gal was greatly reduced when conducted at temperatures other than room temperature. It was particularly noted that at 4° C. the binding was the lowest, this may have been due to precipitation of β-gal at these temperatures. The lower maximum binding that occurred at 37° C. was attributed to the aggregation of the beads at this temperature. The beads tended to clump together in large groups, which minimised the surface area on the beads to which the β-gal could bind.

From the data in Table 8 it is apparent that the maximal binding ($q_m$) dropped by approximately 35 μg β-gal per mg beads at 4° C. and by 25 μg β-gal per mg beads at 37° C. These temperatures are therefore not suitable for maximum protein binding.

The data was analysed with the use of the two separate isotherms. The data showed that the adsorption of β-gal to the beads, despite being reduced, again fitted the Langmuir-Freundlich equation with higher accuracy than the Langmuir equation.

TABLE 8

Maximal binding, Langmuir-Freundlich coefficient (n) and dissociation constants of the wildtype and E537D mutant β-gal at 4 and 37° C. The values obtained at 25° C. are added for comparison

| Enzyme | Temperature (° C.) | $q_m$ (μg β-gal/mg beads) | n | $K_d$ (MM) |
|---|---|---|---|---|
| Wildtype | 4 | 12.12 ± 1.040 | 4.5 ± 2.604 | 0.024 ± 0.0062 |
|  | 25 | 45.88 ± 1.422 | 2.29 ± 0.241 | 0.34 ± 0.0022 |
|  | 37 | 23.79 ± 2.023 | 2.245 ± 0.68 | 0.029 ± 0.005 |
| E537D mutant | 4 | 9.575 ± 0.877 | 3.894 ± 1.789 | 0.03 ± 0.0045 |
|  | 25 | 47.81 ± 1.273 | 2.21 ± 0.246 | 0.48 ± 0.003 |
|  | 37 | 19.26 ± 1.197 | 4.050 ± 1.362 | 0.033 ± 0.0039 |

3.5 Effect of Time on Adsorption

Figure 27:
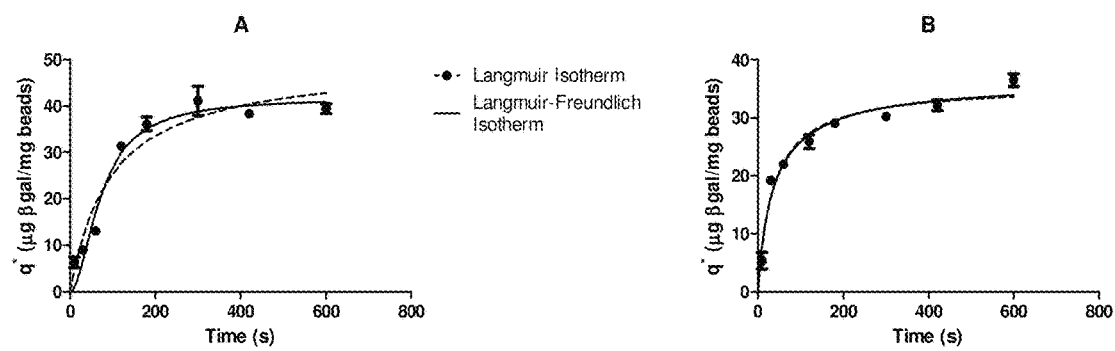
FIG. 27: Time dependence of adsorption isotherms using the Langmuir (dotted line) and Langmuir-Freundlich isotherms (solid line). A: Wildtype. B: E537D mutant. Maximum adsorption was achieved after 5 min incubation.

The optimal incubation time needed for binding was established so that a complete and optimised binding protocol for downstream applications could be established. The manufacturer's protocol suggested a 5 min incubation time for adequate binding. Since β-gal is a relatively large protein (464 kDa), the incubation time was increased to 10 min for the assay. As can be seen by FIG. 27 maximal binding had occurred after 5 min which agreed with the manufacturer's information. The incubation time for the binding when applied to downstream applications was increased to 10 min as a precaution and to ensure that maximal binding took place. The binding was analysed with the two isotherm models and the Langmuir-Freundlich equation again showed a better fit.

4 Characterisation of Immobilised β-Gal: Enzyme Activity and Lactose Binding 4.1 ONPG Activity Assay The immobilisation of a protein on a solid support matrix can change its activity due to sterical hinderance and/or blocking of the active site. Once β-gal was immobilised it was necessary to determine the effect that the immobilisation had on the activity of the enzyme. The wildtype β-gal immobilised on the beads was assayed for activity with the use of ONPG as previously discussed. Since the E537D mutant has an activity that is 115× slower than the wildtype β-gal, the quantity required for an enzyme assay of the immobilized mutant was too large as the beads were too optically dense to detect a colour change on the spectrophotometer. The quantity needed for the immobilised wildtype assay was significantly smaller and the colour change, effected by the wildtype enzyme immobilised on beads, could be accurately recorded.

Figure 28:
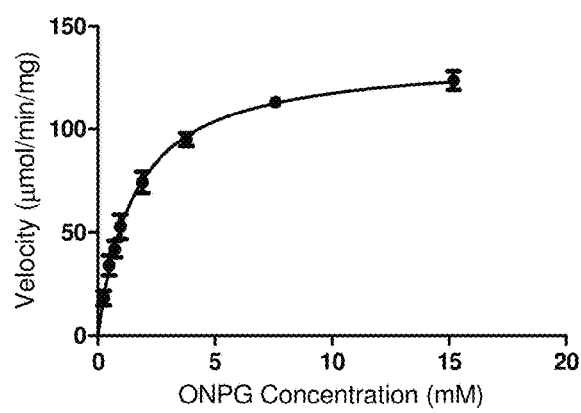
FIG. 28: Michaelis-Menten graph of the ONPG activity assay of the immobilised wildtype β-gal. The $V_{max}$ was 135 μmol/min/mg and the $K_m$ was 1.53 mM representing a decreased activity and affinity for substrate compared to the free enzyme.

The Michaelis-Menten graph, generated from the immobilised wildtype activity assay using ONPG as substrate, is shown in FIG. 28. The immobilisation of β-gal had a significant effect on the enzyme activity. The $V_{max}$ dropped from 230 μmol/min/mg for the free enzyme to 135 μmol/min/mg for the immobilised enzyme. The $K_m$ increased from 0.22 mM for the free enzyme to 1.53 mM for the immobilised enzyme indicating that the immobilisation of the wildtype β-gal significantly decreased the activity and affinity of the enzyme towards the substrate. As the wildtype and the E537D mutant β-gal are structurally closely related it was assumed that the effect of immobilisation on the mutant activity will be similar. These results are most likely due to unfavourable positioning of the β-gal during immobilisation.

4.2 Radioactive Lactose Binding Assay

Figure 29:
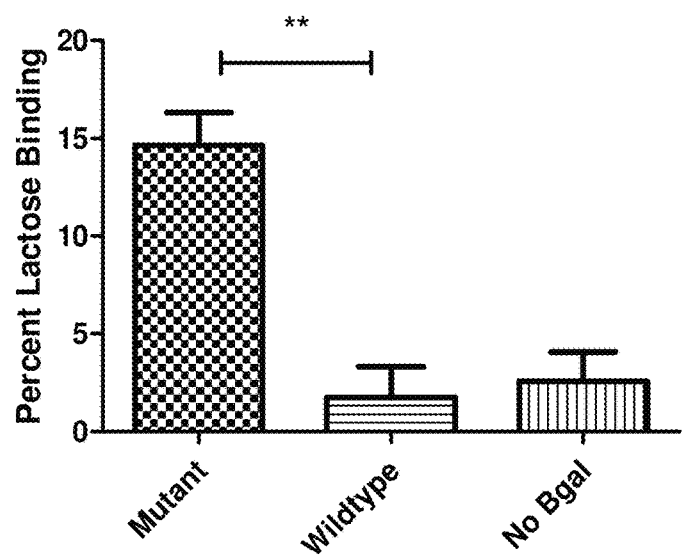
FIG. 29: Percentage binding of lactose from solution by immobilised β-gal and the E537D mutant. The mutant was able to bind approximately 15% of the lactose present. The immobilised wildtype and naked beads were not able to bind lactose from the solution. Graph Pad Prism® software was used for statistical analysis. Columns were compared by a one-way ANOVA, followed by Bonferroni's multiple comparison test (**$P<0.005$).

The immobilised β-gal was subsequently tested for its ability to bind and remove lactose from solution. The amount of lactose bound was calculated from the reduction in signal of the supernatant removed from the beads, relative to the signal obtained by analyses of the original solution. The results from the radioactive binding assay are shown in FIG. 29. The immobilised E537D mutant was able to remove approximately 15% of the $^{14}C$ lactose from solution. The immobilised wildtype enzyme bound approximately 2% of the $^{14}C$ lactose in the solution which was an insignificant background signal. It is apparent that the amount of lactose bound by the immobilised E537D mutant bound was significantly more than the lactose bound by the immobilised wildtype. As control naked MNPs were incubated with the $^{14}C$ lactose. The signal obtained with the naked MNPs was similar to the signal obtained with the wildtype and considered insignificant.

4.3 Partition HPLC 4.3.1 Determination of Retention Times

Figure 30:
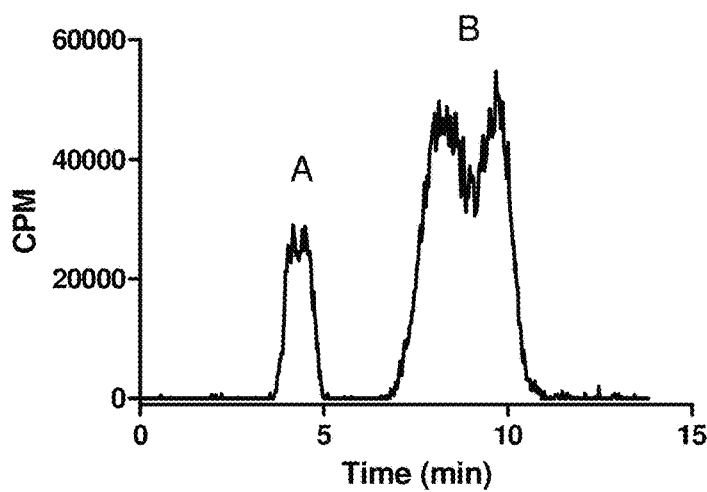
FIG. 30: Partition HPLC separation of glucose (A) and lactose (B) on a Carbohydrate Analysis Column.

The carbohydrate analysis column used was designed for the separation of low molecular weight carbohydrates such as mono-, di- and trisaccharides. The retention time of the $^{14}C$ glucose standard was 4 min while for the $^{14}C$ lactose standard, a broad double peak was observed eluting between 8 and 10 min (FIG. 30). The $^{14}C$ lactose doublet can be ascribed to the presence of the naturally occurring α- and β-isomers (60:40) present in the lactose solution at room temperature. The isomers are separated as β-lactose is more soluble in water than the α isomer (37). When $^{14}C$ lactose is hydrolysed by β-gal it forms $^{14}C$ glucose and a non-radioactive galactose unit as only the glucose of lactose is labelled on C-1.

4.3.2 Analysis of Binding Assay

Figure 31:
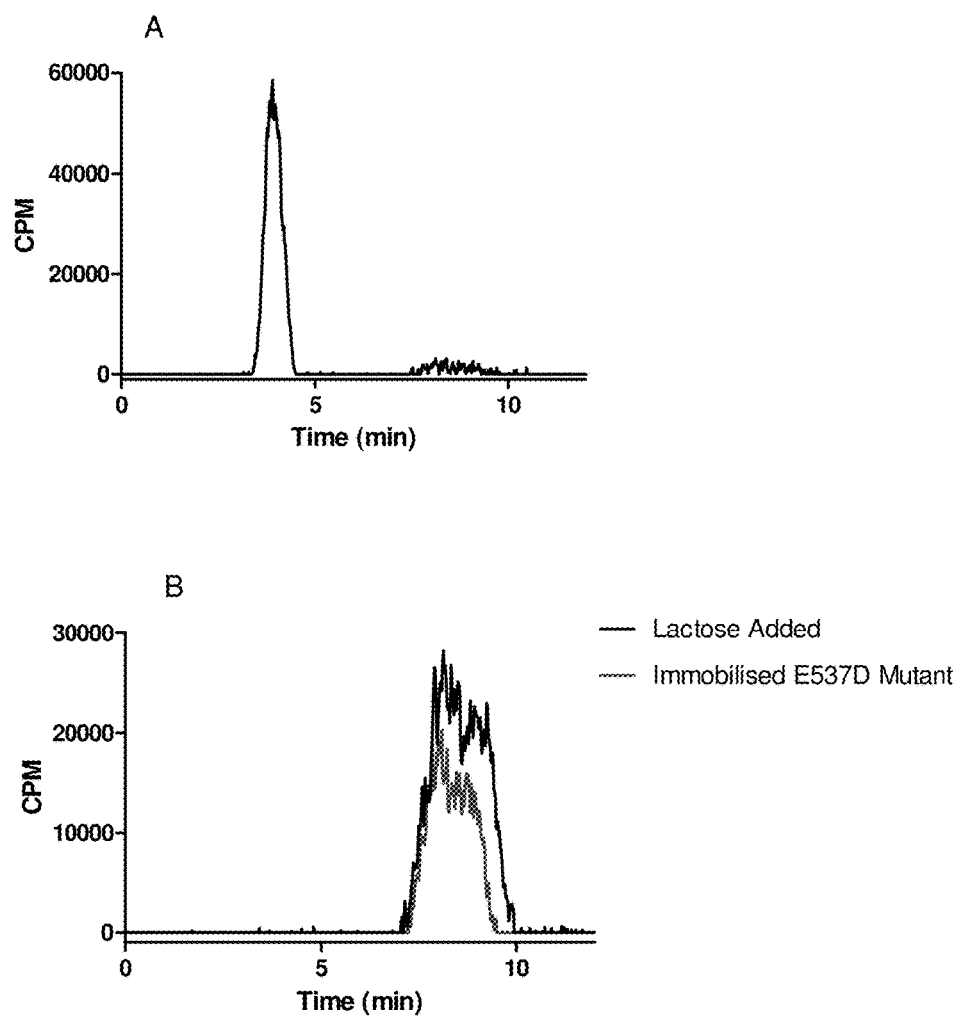
FIG. 31: Partition HPLC chromatogram with a Carbohydrate Analysis column of $^{14}$C lactose binding. A: Immobilised Wildtype β-gal. B: Immobilised E537D Mutant β-gal.

The lactose binding assay was repeated and the supernatants were analysed by HPLC. The chromatograms are shown in FIG. 31. FIG. 31A represents the analysis of the supernatant removed from beads containing immobilised wildtype β-gal and FIG. 31B represents the supernatant removed from beads containing immobilised E537D mutant β-gal. The supernatant removed from beads containing the immobilised wildtype enzyme yielded a chromatogram with a single peak at 4 min corresponding to $^{14}C$ glucose, indicating that the immobilised wildtype β-gal hydrolysed the lactose completely to glucose and galactose and can therefore not bind any lactose for removal from solution.

The dark black line in FIG. 31B represents the chromatogram of a total of 2 nmoles of $^{14}C$ lactose (the lactose solution used in the binding experiment) injected in a total volume of 20 ul. The supernatant of the immobilised E537D mutant from the binding assay yielded the chromatogram represented by the grey line seen in FIG. 31B. From this chromatogram, it is apparent that the immobilised E537D mutant β-gal was able to bind, and remove, a significant amount of lactose from the original lactose solution. It is important to note that there is no peak at 4 min, corresponding to glucose, indicating that the lactose had not been hydrolysed to galactose and glucose during the course of the binding experiment. Integration of the areas under the peaks, shown in FIG. 31, allowed for the quantification of the lactose bound and indicated that 43%, or 0.086 nmoles of the lactose was removed from the original solution containing 2 nmoles of $^{14}$C lactose. Therefore 1 mg of the E537D mutant β-gal immobilised on Dynabeads® (HIPD) was able to remove 0.086 nmol $^{14}$C lactose. These results are in agreement with the idea that the E537D mutant would be able to bind lactose effectively and remove it from solution without hydrolysing the substrate for a certain time frame.

Figure 32:
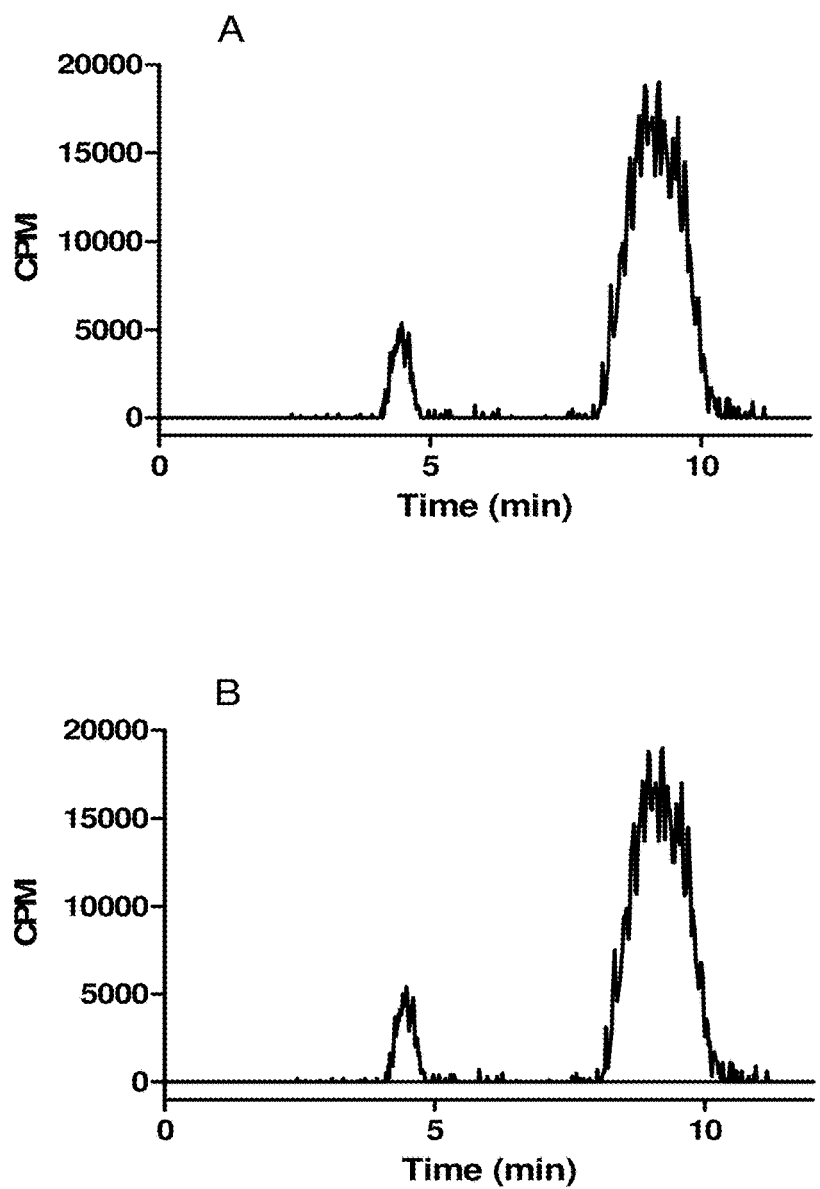
FIG. 32: Partition HPLC chromatogram with a Carbohydrate Analysis column of the effect of time on $^{14}$C lactose binding assay of the immobilised E537D mutant β-gal. A: 20 min. B: 60 min.

Since the E537D mutant retains a low level of activity, hydrolysis of lactose to galactose and glucose will still take place. The lactose binding assay was therefore repeated and the incubation time was increased to determine the time required for the mutant to produce glucose that could be detected by HPLC. After 20 min (Chromatogram A, FIG. 32) a relatively small glucose peak appeared at 4 min with the lactose peak still prominent. After an hour the glucose peak had increased significantly and there was a corresponding decrease in the lactose peak, as shown in FIG. 32B. After three hours lactose could still be detected (results not shown), but the majority of the substrate had been converted to glucose. These results clearly indicated that the immobilised E537D mutant β-gal could indeed hydrolyse lactose, albeit at a significantly lower rate than the immobilised wild type enzyme. This activity would serve to simultaneously sweeten the milk while also removing lactose.

CONCLUSIONS

It has been demonstrated herein that protein functionalised MNPs can be used for bioseparations, and in particular for separating maltose and lactose from solution in a single step. The removal of lactose from milk, with the use of a mutated β-gal immobilised on MNPs, holds great promise for the production of lactose free milk on an industrial scale and relatively simply. In addition, the amount of lactose that needs to be converted to glucose and galactose to retain the desired sweetness of the lactose free milk can be controlled in the method of the present invention, and it is anticipated that the resulting product will be more acceptable to consumers than the lactose free products currently on the market.

REFERENCES

1. Medintz I L, Deschamps J R. Maltose-binding protein: A versatile platform for prototyping biosensing. Curr Opin Biotechnol. 2006; 17(1):17-27.
2. Laurent S, Forge D, Port M, Roch A, Robic C, Vander Elst L. Magnetic iron oxide nanoparticles: Synthesis, stabilization, vectorization, physicochemical characterizations and biological applications. Chem Rev. 2008; 108(6):2064-110.
3. Rui H, Xing R, Xu Z, Hou Y, Goo S, Sun S. Synthesis, functionalization, and biomedical applications of multifunctional magnetic nanoparticles. Adv Mater. 2010; 22(25):2729-42.
4. Lamer V K, Dinegar R H. Theory, production and mechanism of formation of monodispersed hydrosols. J Am Chem Soc. 1950; 72(11):4847-54.
5. de Dios A S, Diaz-Garcia M E. Multifunctional nanoparticles: Analytical prospects. Anal Chim Acta. 2010; 666 (1-2):1-22.
6. Yu C, Oduro W, Tam K, Tsang E S C. Chapter 10 some applications of nanoparticles; 2008 [cited 23 Jun. 2011].
7. Husain Q. β Galactosidases and their potential applications: A review. Crit Rev Biotechnol. 2010; 30(1):41-62.
8. Panesar P S, Panesar R, Singh R S, Kennedy J F, Kumar H. Microbial production, immobilization and applications of β-D-galactosidase. Journal of Chemical Technology and Biotechnology. 2006; 81(4):530-43.
9. Sheik Asraf S, Gunasekaran P. Current trends in beta-galactosidase research and application. In: Current Research, Technology and Education Topics in Applied Microbiology and Microbial Biotechnology; 2010. p. 880.
10. Neri D F M, Balcao V M, Carneiro-da-Cunha M G, Carvalho Jr. L B, Teixeira J A. Immobilization of β-galactosidase from kluyveromyces lactis onto a polysiloxane-polyvinyl alcohol magnetic (mPOS-PVA) composite for lactose hydrolysis. Catal Commun. 2008; 9(14):2334-9.
11. Yuan J, Martinez-Bilbao M, Huber R E. Substitutions for glu-537 of β-galactosidase from escherichia coli cause large decreases in catalytic activity. Biochem J. 1994; 299(2):527-31.
12. Rao S V, Anderson K W, Bachas L G. Oriented immobilization of proteins. Mikrochim Acta. 1998; 128(3-4):127-43.
13. Hernandez K, Fernandez-Lafuente R. Control of protein immobilization: Coupling immobilization and site-directed mutagenesis to improve biocatalyst or biosensor performance. Enzyme Microb Technol. 2011; 48(2):107-22.
14. Neri D F M, Balcäo V M, Dourado F O Q, Oliveira J M B, Carvalho Jr. L B, Teixeira J A. Galactooligosaccharides production by β-galactosidase immobilized onto magnetic polysiloxane-polyaniline particles. React Funct Polym. 2009; 69(4):246-51.
15. Nilsson J, Ståhl S, Lundeberg J, Uhlén M, Nygren P. Affinity fusion strategies for detection, purification, and immobilization of recombinant proteins. Protein Expr Purif. 1997; 11(1):1-16.
16. Josten A, Meusel M, Spener F, Haalck L. Enzyme immobilization via microbial transglutaminase: A method for the generation of stable sensing surfaces. Journal of Molecular Catalysis—B Enzymatic. 1999; 7(1-4):57-66.
17. Hannig C, Spitzmüller B, Hoth-Hannig W, Hannig M. Targeted immobilisation of lysozyme in the enamel pellicle from different solutions. Clin Oral Investig. 2011; 15(1):65-73.
18. Nakanishi K, Sakiyama T, Kumada Y, Imamura K, Imanaka H. Recent advances in controlled immobilization of proteins onto the surface of the solid substrate and its possible application to proteomics. Current Proteomics. 2008; 5(3):161-75.
19. Cronan Jr. J E. Biotination of proteins in vivo. A post-translational modification to label, purify, and study proteins. J Biol Chem. 1990; 265(18)10327-33.
20. Li Y, Bi L, Zhang X, Zhou Y, Zhang J, Chen Y. Reversible immobilization of proteins with streptavidin affinity tags on a surface plasmon resonance biosensor chip. Analytical and Bioanalytical Chemistry. 2006; 386 (5):1321-6.
21. Porath J. Immobilized metal ion affinity chromatography. Protein Expr Purif. 1992; 3(4):263-81.

22. Porath J, Carlsson J, Olsson I, Belfrage G. Metal chelate affinity chromatography, a new approach to protein fractionation. Nature. 1975; 258(5536):598-9.
23. Bertz, M, Rief, M. 2009. Ligand Binding Mechanics of Maltose Binding Protein. J. Mol. Biol. 393:1097-1105.
24. Daabrowski, S S, Sobiewska, G, Maciuńska, J, Synowiecki, J, Kur, J. 2000. Cloning, expression, and purification of the His6-tagged thermostable β-galactosidase from *Pyrococcus woesei* in *Escherichia coli* and some properties of the isolated enzyme. Protein Expr. Purif. 19:107-112.
25. Huber, R E, Gupta, M N, Khare, S K. 1994. The active site and mechanism of the β-galactosidase from *Escherichia coli*. Int. J. Biochem. 26:309-318.
26. Juers, D H, Heightman, T D, Vasella, A, McCarter, J D, Mackenzie, L, Withers, S G, Matthews, B W. 2001. A structural view of the action of *Escherichia coli* (lacZ) β-galactosidase. Biochemistry (N.Y.). 40:14781-14794.
27. Juers, D H, Jacobson, R H, Wigley, D, Zhang, X-, Huber, R E, Tronrud, D E, Matthews, B W. 2000. High resolution refinement of β-galactosidase in a new crystal form reveals multiple metal-binding sites and provides a structural basis for α-complementation. Protein Science. 9:1685-1699.
28. Juers, D H, Rob, B, Dugdale, M L, Rahimzadeh, N, Giang, C, Lee, M, Matthews, B W, Huber, R E. 2009. Direct and indirect roles of His-418 in metal binding and in the activity of β-galactosidase (*E. coli*). Protein Science. 18:1281-1292.
29. Matthews, B W. 2005. The structure of *E. coli* β-galactosidase. Comptes Rendus—Biologies. 328:549-556.
30. Kuo, W-K, Chase, H A. 2011. Exploiting the interactions between poly-histidine fusion tags and immobilized metal ions. Biotechnol. Lett. 33:1075-1084.
31. Block, H, Maertens, B, Spriestersbach, A, Brinker, N, Kubicek, J, Fabis, R, Labahn, J, Schafer, F. 2009. Chapter 27 Immobilized-Metal Affinity Chromatography (IMAC). A Review. Methods in Enzymology. 463:439-473.
32. Ho, C-, Limberis, L, Caldwell, K D, Stewart, R J. 1998. A metal-chelating pluronic for immobilization of histidine-tagged proteins at interfaces: Immobilization of firefly luciferase on polystyrene beads. Langmuir. 14:3889-3894.
33. Pessela, B C C, Mateo, C, Carrascosa, A V, Vian, A, Garcia, J L, Rivas, G, Alfonso, C, Guisan, J M, Fernandez-Lafuente, R. 2003. One-step purification, covalent immobilization, and additional stabilization of a thermophilic poly-his-tagged β-galactosidase from *Thermus* sp. strain T2 by using novel heterofunctional chelate—Epoxy sepabeads. Biomacromolecules. 4:107-113.
34. Xu, C, Xu, K, Gu, H, Zhong, X, Guo, Z, Zheng, R, Zhang, X, Xu, B. 2004. Nitrilotriacetic Acid-Modified Magnetic Nanoparticles as a General Agent to Bind Histidine-Tagged Proteins. J. Am. Chem. Soc. 126:3392-3393.
35. Ladero, M, Santos, A, Garcia, J L, Garcia-Ochoa, F. 2001. Activity over lactose and ONPG of a genetically engineered β-galactosidase from *Escherichia coli* in solution and immobilized: Kinetic modelling. Enzyme Microb. Technol. 29:181-193.
36. Merino G, Shuman H A. Unliganded maltose-binding protein triggers lactose transport in an *escherichia coli* mutant with an alteration in the maltose transport system. J Bacteriol. 1997; 179(24):7687-94.
37. Drapier-Beche, N, Fanni, J, Parmentier, M. 1999. Physical and chemical properties of molecular compounds of lactose. J. Dairy Sci. 82:2558-2563.

The invention claimed is:

1. A method for removing lactose from a lactose-containing solution, the method comprising the steps of:
   a. adding to the lactose-containing solution one or more magnetic nanoparticles onto which a β-galactosidase enzyme is immobilised, the β-galactosidase enzyme having at least one mutation which reduces the lactose hydrolysing activity of the β-galactosidase relative to the immobilised wild-type β-galactosidase, wherein the mutation is a Glu-537 mutation, a Glu-461 mutation, or a His-418 mutation, or any combination thereof;
   b. allowing the β-galactosidase enzyme on the magnetic nanoparticles to bind lactose from the solution; and
   c. magnetically separating the magnetic nanoparticles with the immobilised β-galactosidase enzyme including bound lactose from the solution, thereby removing the lactose which is bound to the β-galactosidase enzyme on the magnetic nanoparticles wherein more than 50% of any lactose present is removed from the solution.

2. The method as claimed in claim 1, wherein there is no substantial change in the sweetness of the solution by removal of the lactose without being hydrolysed.

3. The method as claimed in claim 1, wherein the lactose-containing solution is milk or a dairy product.

4. The method as claimed in claim 1, wherein the β-galactosidase is an *E. coli* β-galactosidase.

5. The method as claimed in claim 1, wherein the Glu-537 mutation is an E537D mutation.

6. The method as claimed in claim 1, wherein the β-galactosidase contains an affinity tag at or near the N- or C-terminus.

7. The method as claimed in claim 6, wherein the affinity tag is selected from the group consisting of a polyhistidine tag (His-tag), a transglutaminase, a glutathione S-transferase, a FLAG, a biotin, a maltose binding protein, a glycoprotein and a cysteine-mediated site-directed mutagenesis product.

8. The method as claimed in claim 1, wherein the magnetic nanoparticle has a coating.

9. The method as claimed in claim 1, wherein the lactose is removed from the solution without being hydrolysed.

10. The method as claimed in claim 1, wherein the magnetic nanoparticles with immobilised β-galactosidase enzyme including bound lactose are removed from the solution upon the onset of glucose formation.

11. The method as claimed in claim 1, wherein the mutation is a Glu-537 mutation.

12. The method as claimed in claim 1, wherein over 90% of any lactose present is removed from the solution.

* * * * *

SEQUENCE LISTING

<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Primer sequence

<400> SEQUENCE: 1
gtcatgacca tgattacgga ttcac                                          25

<210> SEQ ID NO 2
<211> LENGTH: 34
<212> TYPE: DNA
<213> ORGANISM: Artificial Sequence
<220> FEATURE:
<223> OTHER INFORMATION: Primer sequence

<400> SEQUENCE: 2
ctgcccggat cctattattt ttgacaccag acca                                34

<210> SEQ ID NO 3
<211> LENGTH: 34
<212> TYPE: DNA
<213> ORGANISM: Artificial Sequence
<220> FEATURE:
<223> OTHER INFORMATION: Primer sequence

```
-continued

<400> SEQUENCE: 3
cgcgcccgct gatcctttgc gactacgccc acgc                                34

<210> SEQ ID NO 4
<211> LENGTH: 30
<212> TYPE: DNA
<213> ORGANISM: Artificial Sequence
<220> FEATURE:
<223> OTHER INFORMATION: Primer sequence

<400> SEQUENCE: 4
tcgcaaagga tcagcgggcg cgtctctcca                                     30

<210> SEQ ID NO 5
<211> LENGTH: 19
<212> TYPE: DNA
<213> ORGANISM: Artificial Sequence
<220> FEATURE:
<223> OTHER INFORMATION: Primer sequence

<400> SEQUENCE: 5
tatggctagc atgactggt                                                 19

<210> SEQ ID NO 6
<211> LENGTH: 17
<212> TYPE: DNA
<213> ORGANISM: Artificial Sequence
<220> FEATURE:
<223> OTHER INFORMATION: Primer sequence

<400> SEQUENCE: 6
gatttatctg tatcagg                                                   17

<210> SEQ ID NO 7
<211> LENGTH: 480
<212> TYPE: DNA
<213> ORGANISM: Escherichia coli

<400> SEQUENCE: 7
taatcacgac gcgctgtatc gctggatcaa atctgtcgat ccttcccgcc cggtgcagta    60
tgaaggcggc ggagccgaca ccacggccac cgatattatt tgcccgatgt acgcgcgcgt   120
ggatgaagac cagcccttcc cggctgtgcc gaaatggtcc atcaaaaaat ggctttcgct   180
acctggagag acgcgcccgc tgatcctttg cgaatacgcc cacgcgatgg gtaacagtct   240
tggcggtttc gctaaatact ggcaggcgtt tcgtcagtat ccccgtttac agggcggctt   300
cgtctgggac tgggtggatc agtcgctgat taaatatgat gaaaacggca acccgtggtc   360
ggcttacggc ggtgattttg gcgatacgcc gaacgatcgc cagttctgta tgaacggtct   420
ggtctttgcc gaccgcacgc cgcatccagc gctgacggaa gcaaaacacc agcagcagtt   480
```